US008785119B2

(12) United States Patent
Cooperman et al.

(10) Patent No.: US 8,785,119 B2
(45) Date of Patent: Jul. 22, 2014

(54) FLUORESCENT LABELING OF TRANSFER RNA AND STUDY OF PROTEIN SYNTHESIS

(75) Inventors: Barry S. Cooperman, Penn Valley, PA (US); Zeev Smilansky, D.N. Emek Sorek (IL); Yale E. Goldman, Merion, PA (US); Dongli Pan, Brookline, MA (US)

(73) Assignees: Anima Cell Metrology, Basking Ridge, NJ (US); The Trustees of the University of Pennsylvania, Philadelphia, PA (US)

( * ) Notice: Subject to any disclaimer, the term of this patent is extended or adjusted under 35 U.S.C. 154(b) by 669 days.

(21) Appl. No.: 12/664,952

(22) PCT Filed: Jun. 20, 2008

(86) PCT No.: PCT/US2008/067735
§ 371 (c)(1),
(2), (4) Date: Jan. 13, 2011

(87) PCT Pub. No.: WO2009/002866
PCT Pub. Date: Dec. 31, 2008

(65) Prior Publication Data
US 2011/0262899 A1 Oct. 27, 2011

Related U.S. Application Data

(60) Provisional application No. 60/945,771, filed on Jun. 22, 2007.

(51) Int. Cl.
*C12Q 1/68* (2006.01)
*C07H 21/00* (2006.01)

(52) U.S. Cl.
USPC .......................................... 435/6.1; 536/22.1

(58) Field of Classification Search
USPC .......................................... 435/6.1; 536/22.1
See application file for complete search history.

(56) References Cited

U.S. PATENT DOCUMENTS

| 5,648,269 A * | 7/1997 | Lakowicz et al. ............... 436/68 |
| 2003/0219783 A1 | 11/2003 | Puglisi et al. |
| 2004/0023256 A1 | 2/2004 | Puglisi et al. |

OTHER PUBLICATIONS

Negrutskii et al., Supramolecular organization of the mammalian translation system. PNAS 91 : 964 (1994).*
Rodina et al., Transient conformational states of Aminoacyl-tRNA during ribosome binding catalyzed by elongation Factor Tu. Biochemistry 33 :12267 (1994).*
"Hydrazines, Hydroxylamines and Aromatic Amines for Modifying Aldehydes and Ketones", Molecular Probes Handbook, Section 3.2, 1-11, Retrieved online from the Internet on Apr. 5, 2005.
Betteridge et al., "Fluorescent labeling of tRNAs for dynamics experiments", RNA. Sep. 2007, 13(9), 1594-1601.
Bieling et al., "Peptide bond formation does not involve acid-base catalysis by ribosomal residues", Nat Struct Mol Biol., May 2006, 13(5), 423-428.
Bishop et al., "Identification of the tRNA-dihydrouridine synthase family", J Biol Chem., Jul. 12, 2002, 277(28), 25090-25095.
Blanchard et al., "tRNA dynamics on the ribosome during translation", Proc Natl Acad Sci USA, Aug. 31, 2004, 707(35), 12893-12898.
Blanchard et al., "tRNA selection and kinetic proofreading in translation", Nat Struct Mol Biol, Oct. 2004, 11(10), 1008-1014.
Boonacker et al., "Enzyme cytochemical techniques for metabolic mapping in living cells with special reference to proteolysis", J Histochem Cytochem, Dec. 2001, 49(12), 1473-1486.
Cerutti et al., "Selective reduction of yeast transfer ribonucleic acid with sodium borohydride", J Mol Biol, May 28, 1967, 26(1), 55-66.
Cochella et al., "An active role for tRNA in decoding beyond codon:anticodon pairing", Science, May 20, 2005, 308(5725), 1178-1180.
Grigoriadou et al., "A quantitative kinetic scheme for 70 S translation initiation complex formation", J Mol Biol., Oct. 26, 2007, 373(3), 562-572.
Grigoriadou et al., "The Translational Fidelity Function of IF3 During Transition from the 30 SInitiation Complex to the 70 S Initiation Complex", J Mol Biol., Oct. 26, 2007, 373(3), 551-556.
Hirsh, "Tryptophan transfer RNA as the UGA suppressor", J Mol Biol., Jun. 14, 1971, 58(2), 439-444.
Horobin et al., "Fluorescent cationic probes for nuclei of living cells: why are they selective? A quantitative structure-activity relations analysis", Histochem Cell Biol, Aug. 11, 2006, 126(22), 165-175.
Hou et al., "Isolation of a site-specifically modified RNA from an unmodified transcript", Nucleic Acids Res, Jan. 2006, 34(3), 1-6.
Hou, "The tertiary structure of tRNA and the development of the genetic code", Trends Biochem Sci, Oct. 1993, 18(10), 362-364.

(Continued)

*Primary Examiner* — Ethan C Whisenant
(74) *Attorney, Agent, or Firm* — Baker & Hostetler LLP

(57) ABSTRACT

Provided are methods for labeling transfer RNA comprising replacing the uracil component of a dihydrouridine of said transfer RNA with a fluorophore. The disclosed methods may comprise fluorescent labeling of natural tRNAs (i.e., tRNAs that have been synthesized in a cell, for example, in a bacterium, a yeast cell, or a vertebrate cell) at dihydrouridine (D) positions, or fluorescent labeling of synthetic tRNAs. In another aspect, the present invention provides methods for assessing protein synthesis in a translation system comprise providing a tRNA having a fluorophore substitution for the uracil component of a dihydrouridine in a D loop of the tRNA; introducing the labeled tRNA into the translation system; irradiating the translation system with electromagnetic radiation, thereby generating a fluorescence signal from the fluorophore; detecting the fluorescence signal; and, correlating the fluorescence signal to one or more characteristics of the protein synthesis in the translation system. The disclosed methods are useful in single molecule as well as in ensemble settings.

17 Claims, 5 Drawing Sheets

(56) References Cited

OTHER PUBLICATIONS

Jacobson et al., "Determination of 5, 6-dihydrouridine in ribonucleic acid", Anal Biochem, Apr. 1970, 34(2), 459-469.

Jencks, "Mechanism and catalysis of simple carbonyl group reactions", Prog. Phys. Org. Chem., (no month available) 1964, 2, 63-128.

Korostelev et al., "Crystal structure of a 70S ribosome- tRNA complex reveals functional interactions and rearrangements", Cell, Sep. 22, 2006, 126(6), 1065-1077.

Lee et al., "New energy transfer dyes for DNA sequencing", Nucleic Acids Res., Jul. 15, 1997, 25(14), 2816-2822.

Levrand et al., "Controlled Release of Volatile Aldehydes and Ketones from Dynamic Mixtures Generated by Reversible Hydrazone Formation", Helv Chim Acta, Dec. 14, 2007, 90(12), 2281-2314.

Lipman et al., "Prevention of mis-aminoacylation of a dual- specificity aminoacyl-tRNA synthetase" J Mol Biol, Feb. 1, 2002, 315(5), 943-949.

Liu et al., "*Escherichia coli* proline tRNA synthetase is sensitive to changes in the core region of tRNA(Pro)", Biochemistry, Oct. 1994, 33(42), 12708-12714.

McIntosh et al., "Initiation of protein synthesis with fluorophore-Met-tRNA(f) and the involvement of IF-2", Biochimie, Feb. 2000, 82(2), 167-174.

Munro et al., "Identification of two distinct hybrid state intermediates on the ribosome", Mol Cell, Feb. 23, 2007, 25(4), 505-517.

Negrutskii et al., "Channeling of aminoacyl-tRNA for protein synthesis in vivo", Proc Natl Acad Sci USA, Jun. 1, 1991, 88(11), 4991-4995.

Pan et al., "Kinetically competent intermediate(s) in the translocation step of protein synthesis", Mol Cell, Feb. 23, 2007, 25(4), 519-529.

Pan et al., "Perturbation of the tRNA tertiary core differentially affects specific steps of the elongation cycle", J Biol Chem, Jun. 27, 2008, 283(26), 18431-18440.

Pan et al., "Rapid ribosomal translocation depends on the conserved 18-55 base pair in P-site transfer RNA", Nat Struct Mol Biol, Apr. 2006, 13(4), 354-359.

Pape et al., "Complete kinetic mechanism of elongation factor Tu-dependent binding of aminoacyl-tRNA to the a site of the *E. coli* ribosome", Embo J., Oct. 1998, 17, 7490-7497.

Rodnina et al., "Hydrolysis of GTP by elongation factor G drives tRNA movement on the ribosome", Nature, Jan. 2, 1997, 385(6611), 37-41.

Sako et al., "A novel therapeutic approach for genetic diseases by introduction or suppressor tRNA", Nucleic Acids Symposium Series, (no month available) 2006, 50(1), 239-240.

Sampson et al., "Nucleotides in yeast tRNAPhe required for the specific recognition by its cognate synthetase", Science, Mar. 10, 1989, 243(4896), 1363-1366.

Savelsbergh et al., "An elongation factor G-induced ribosome rearrangement precedes tRNA-mRNA translocation", Mol Cell, Jun. 2003, 11(6), 1517-1523.

Scala-Valero et al., "Synthesis of Isomers of Rhodamine 575 and Rhodamine 6G as New Laser Dyes", Tet Lett, Jun. 25, 1999, 40(26), 4803-4806.

Selmer et al., "Structure of the 70S ribosome complexed with mRNA and tRNA", Science, Sep. 29, 2006, 313(5795), 1935-1942.

Sprinzl et al., "Compilation of tRNA sequences and sequences of tRNA genes", Nucleic Acids Res, Jan. 1, 1998, 26(1), 148-153.

Thiebe et al., "A specific modification next to the anticodon of phenylalanine transfer ribonucleic acid", Eur J Biochem., Sep. 24, 1968, 5(4), 546-555.

Westhof, "The ribosomal decoding site and antibiotics", Biochimie, Aug. 2006, 88(18), 931-933.

Wintermeyer et al., "Fluorescent Derivatives of Yeast tRNA$^{phe}$", European Journal of Biochemistry, Aug. 1, 1979, 98(2), 465-475.

Wintermeyer et al., "Replacement of odd bases in tRNA by fluorescent dyes", Methods Enzymol, (no month available) 1974, 29(0), 666-673.

Wintermeyer et al., "Replacement of Y base, dihydrouracil, and 7-methylguanine in tRNA by artificial odd bases", FEBS Lett., Nov. 1, 1971, 18(2), 214-218.

Woolhead et al., "Nascent membrane and secretory proteins differ in FRET-detected folding far inside the ribosome and in their exposure to ribosomal proteins", Cell, Mar. 5, 2004, 116(5), 725-736.

Xing et al., "A conserved family of *Saccharomyces cerevisiae* synthases effects dihydrouridine modification of tRNA", RNA, Mar. 2002, 8(3), 370-381.

Xing et al., "The specificities of four yeast dihydrouridine synthases for cytoplasmic tRNAs", J Biol Chem, Apr. 23, 2004, 279(17), 17850-17860.

Yang et al., "Studies of Transfer RNA Tertiary Structure by Singlet-Singlet Energy Transfer", Proc. Nat. Acad. Sci., USA, Jul. 1974, 71(71), 2838-2842.

Yusupov et al, "Crystal Structure of the Ribosome at 5.5 a Resolution", Science, May 4, 2001, 292(5518), 883-896.

Zhang et al., "Synthesis of cysteinyl-tRNACys by a prolyl-tRNA synthetase", RNA Biology, May 2004, 1(1), 35-41.

* cited by examiner

SEQUENCE LISTING

```
<160> NUMBER OF SEQ ID NOS: 2

<210> SEQ ID NO 1
<211> LENGTH: 17
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: m = 2'-O-methyl backbone
<220> FEATURE:
<221> NAME/KEY: misc_feature
<222> LOCATION: (13)..(17)
```

```
<223> OTHER INFORMATION: m = 2'-O-methyl backbone

<400> SEQUENCE: 1
ugcgcuacca agcugcg                                                    17

<210> SEQ ID NO 2
<211> LENGTH: 36
<212> TYPE: RNA
<213> ORGANISM: Artificial Sequence
<220> FEATURE:
<223> OTHER INFORMATION: Synthetic construct

<400> SEQUENCE: 2
gggaaggagg uaaaaauguu uaaacguaaa ucuacu                               36
```

FLUORESCENT LABELING OF TRANSFER RNA AND STUDY OF PROTEIN SYNTHESIS

STATEMENT OF GOVERNMENT SUPPORT

The United States government may have rights in the invention described herein, which was made in part with funding from The National Institutes of Health, Grant Nos. GM66267 and GM71014.

CROSS-REFERENCE TO RELATED APPLICATIONS

This application is the National Stage of International Application No. PCT/US2008/067735, filed Jun. 20, 2008, which claims the benefit of U.S. Provisional Application No. 60/945,771 filed Jun. 22, 2007, the disclosures of which are incorporated herein by reference in their entirety.

FIELD

The invention relates to methods for labeling transfer RNA with a fluorophore, and methods for the study of protein synthesis utilizing a fluorophore-labeled transfer RNA.

BACKGROUND

Decoding of genetic information into protein sequences is a multi-step process that requires specific charging of transfer RNA (tRNA) molecules with their cognate amino acids by their cognate aminoacyl-tRNA synthetases (aaRSs) to form aminoacyl-tRNA (aa-tRNA), specific binding of aa-tRNAs to the ribosomal decoding center programmed with their cognate triplet codons, and large scale movements of tRNAs within the ribosome as they shift progressively from the tRNA entry site (the A-site), to the peptidyl-tRNA site (the P-site), and finally to the tRNA exit site (the E-site), from which tRNA dissociation takes place.

While the elementary steps in elongation have been identified, additional studies will be required to achieve a full understanding of the molecular mechanisms of each step. Of particular interest is the role of tRNAs, which, rather than being passive and rigid substrates for the ribosome, have been more recently implicated as being "active" players in the decoding process (Westhof, 2006), interacting strongly with different sites on the ribosome and undergoing substantial conformational changes in migrating from the A- to P- to E-sites (Korostelev et al., 2006; Selmer et al., 2006). For example, a mutation in the D stem of tRNA$^{Trp}$ (known as the Hirsh suppressor mutation (Hirsh, 1971) has been shown to promote miscoding at the anticodon. Recent kinetic studies show that this mutation specifically accelerates two forward steps on the ribosome: GTP hydrolysis for accommodation of aa-tRNA to the A site and peptide bond formation (Cochella & Green, 2005). Because this mutation is distal from the codon-anticodon interaction, its ability to promote tRNA accommodation and peptide bond synthesis suggests that the tRNA body is in direct communication with both the decoding center of the 30S subunit and the GTPase center of the 50S subunit. Another example is provided by the tertiary core 'elbow' region of tRNA, which is formed by extensive interactions between the D and T-loops. We have demonstrated, using single turnover rapid kinetics measurements (Pan et al., 2006; Pan et al., 2007), that mutations in the conserved G18: U55 base pair interfere with the ribosomal translocation step, particularly for tRNA moving from the P- to the E-site, consistent with X-ray crystallography results showing that position 55 is in direct contact with protein L1 in the E-site (Korostelev et al., 2006).

In existing studies, an important assay for the translocation rate is based on fluorescent changes of modified natural tRNAs, isolated from E. coli or yeast cells, whose D residues have been replaced with proflavin (Wintermeyer & Zachau, 1979; Savelsbergh et al., 2003). However, this approach, as so far applied, suffers from two significant limitations. First, it does not allow direct monitoring of the movements of tRNA mutants on the ribosome. This is because mutant tRNAs, which are prepared by run-off in vitro transcription with T7 RNA polymerase (Sampson et al., 1989), lack D residues. As a result fluorescent A-site tRNA has been used to monitor effects of mutation in P-site tRNA, and fluorescent P-site tRNA to measure effects of mutation in A-site tRNA. Second, proflavin is rapidly photobleached, rendering proflavin-labeled tRNA unsuitable for single molecule experiments in which fluorescent probes are subject to high light fluxes. Interest in overcoming this limitation is high, because recent work has clearly demonstrated the potential of the single-molecule approach to yield more detailed mechanistic information about protein synthesis than is available from ensemble single turnover experiments (Blanchard et al., 2004a; Blanchard et al., 2004b).

The labeling of tRNA has been performed with respect to each of four different components of such molecules: (1) Amino acids. The amino group of Lys-tRNA$^{Lys}$ was labeled with BODIPY FL by displacing its succinimidyl group (Woodhead, 2004), and the amino group of Met-tRNA$^{fMet}$ was acylated and reacted with maleimide to produce fluorophore-Met-tRNA$^{fMet}$, which, however, has reduced activity compared to the unmodified molecule (McIntosh 2000). (2) 4-thioU(8) group. This has been used for the studies of aminoacyl-tRNA binding to the ribosomal A site (Bieling et al, 2006; Blanchard, 2004a,b; Munro, 2007). (3) acp$^3$U47 group. It has only been labeled by the Blanchard group for their FRET studies (Blanchard, 2004a,b; Munro, 2007). (4) Dihydrouridine group. This group has been used to study the kinetics of tRNA binding and movements on the ribosome, but the choice of dye is limited to only proflavin, which, as described above, is very sensitive to environment but is of little use for single molecule studies, which require brighter dyes, or for FRET studies, which require a good donor-acceptor pair.

Since labeled tRNAs are so important for the studies of dynamics of ribosome function it is important to find a universal method of labeling many tRNA species with many different dyes. All the above labeling methods have their limitations. The amine reactive labeling of the amino acid results in tRNAs that have low activities (McIntosh, 2000; Woodhead, 2004). The other three methods are dependent on the existence of the modified group, so they can not be used if a transcribed tRNA, e.g., for the in vitro study of tRNA mutants, is required. For acp$^3$U47, only 5 of the 20 amino acids have tRNAs that have a acp$^3$ modification further limiting its application on other tRNAs. 4-thioU and dihydroU are more prevalent modifications occurring in the 8th position, and D loop, respectively (in E. coli only tRNA$^{Glu}$, tRNA$^{Lys}$, and tRNA$^{Thr}$ do not have a 4-thioU modification, and only tRNA$^{Glu}$ and tRNA$^{Tyr}$ do not have a D modification). In ribosome studies, 4-thio U has been only successfully used with initiator tRNA, and our attempts to label an elongator tRNA proceeded with only modest yields. Furthermore, labeled Tyr-tRNA$^{Tyr}$ showed very poor binding to ribosomes under conditions that are EF-Tu dependent.

Over the last decade, achievements have been realized through the application of new technologies to the life sciences, for example, whole genome sequencing, DNA microarrays, and proteomic high-throughput analysis. The data obtained with these technologies serve to underscore gaps remaining in the cellular information currently available. Two of these gaps are: 1) sensitive and efficient protein identification, and 2) the dynamics of protein expression. Development of methods to detect protein synthesis directly and in real time, identify the amino acid sequence of a protein, and localize such synthesis within a cell (live proteomics) will enable fundamental advances in understanding basic life processes and aid significantly the search for new sources of therapy. See, for example, PCT Published Apps. WO 2004/050825 and WO 2006/228708. Protein synthesis monitoring (PSM) is an analytical method to identify proteins being synthesized on single ribosomes, in live cells, and in real time. In PSM, the protein synthesis apparatus is marked with a unique fluorescent labeling scheme, producing sequence-specific signals that enable protein identification. See, for example, PCT Published App. WO 2005/116252.

The study of cellular dynamics can utilize mRNA profiling in tissues and cells as a primary tool in research and clinical diagnosis. However, mRNA levels are uncertain predictors of protein expression. Current proteomic analysis, based largely on 2D electrophoretic gels, mass spectrometry, and combinatorial arrays, is limited by destructive sample preparation, preventing both the real-time detection of proteins and the elucidation of the dynamics of cellular response to various modulators. A need exists in the art for reagents with increased sensitivity in a system for studying cellular dynamics, such as Protein Synthesis Monitoring (PSM), which can measure protein synthesis by following thousands of labeled ribosomes simultaneously and repeating the measurements at any specific location for hours or days. Fluorescently translation components with increased sensitivity in a protein synthesis monitoring system are needed to provide the ability to record the dynamic patterns of protein synthesis in live cells in vivo, or in vitro.

SUMMARY

The present invention provides efficient methods for fluorescent labeling of transfer RNA (tRNA). The methods for tRNA labeling enable the assessment of protein synthesis in vitro or in vivo in one or more living cells with greater sensitivity that that which was possible in accordance with prior methods, and overcome limitations related to rapid photobleaching of traditional labeled tRNAs, such as proflavin-labeled tRNA. The present methods are useful in experiments to assess protein synthesis directly and in real time. For example, the methods enable the recording of the dynamic patterns of protein synthesis in live cells, including direct monitoring of the movements of tRNA or tRNA mutants on the ribosome. The present methods are useful in single molecule as well as in ensemble settings. Numerous other methods for assessing protein synthesis using the presently-disclosed fluorescently labeled tRNAs are provided herein.

In one aspect, the present invention provides methods for labeling transfer RNA comprising replacing the uracil component of a dihydrouridine of said transfer RNA with a rhodamine fluorophore.

Also disclosed are nucleic acid compositions comprising a transfer RNA molecule including a fluorophore substitution for the uracil component of a dihydrouridine in a D loop of the transfer RNA. The fluorophore preferably bears a primary amino group, and may be, for example, a hydrazide or a rhodamine fluorophore.

The present invention also provides methods for assessing protein synthesis in a translation system. In preferred aspects, such methods comprise providing a tRNA having a fluorophore substitution for the uracil component of a dihydrouridine in a D loop of the tRNA; introducing the labeled tRNA into the translation system; irradiating the translation system with electromagnetic radiation, thereby generating a fluorescence signal from the fluorophore; detecting the fluorescence signal; and, correlating the fluorescence signal to one or more characteristics of said protein synthesis in said translation system.

DETAILED DESCRIPTION

Figure 1:
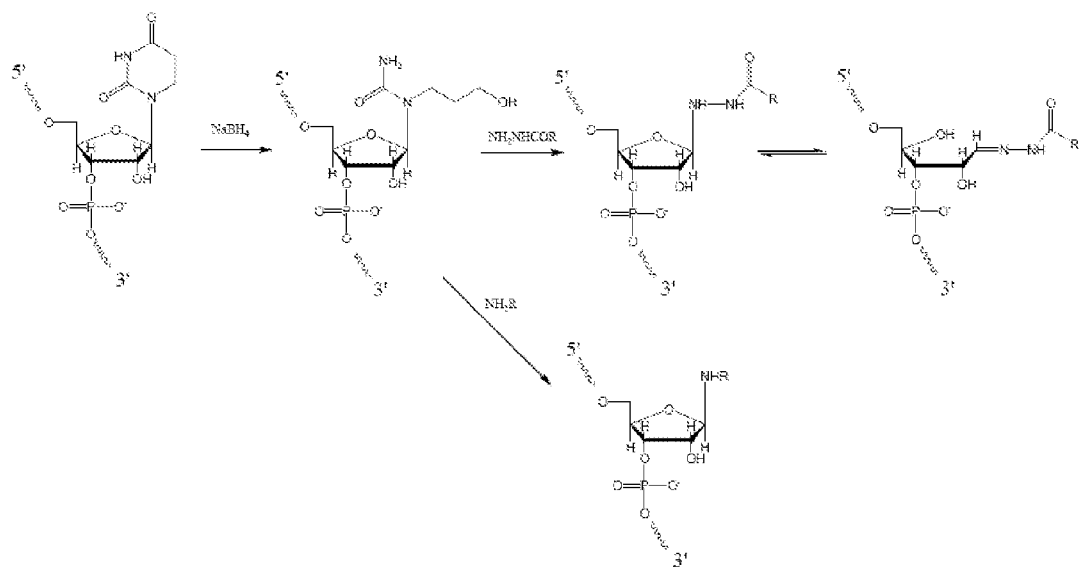
FIG. 1 provides a scheme of an exemplary reaction for the labelling of a D-loop dihydrouradine residue.

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "a translation component" is a reference to one or more of such components and equivalents thereof known to those skilled in the art, and so forth. When values are expressed as approximations, by use of the antecedent "about," it will be understood that the particular value forms another embodiment. As used herein, "about X" (where X is a numerical value) refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable.

The disclosures of each patent, patent application, and publication cited or described in this document are hereby incorporated herein by reference, in their entirety. Full citations for each of the publications cited herein may be found below at paragraph [0092], titled "References Cited."

In accordance with the present invention, provided are methods for labeling transfer RNA comprising replacing the uracil component of a dihydrouridine of said transfer RNA with a fluorophore. The disclosed methods may comprise fluorescent labeling of natural tRNAs (i.e., tRNAs that have been synthesized in a cell, for example, in a bacterium, a yeast cell, or a vertebrate cell) at dihydrouridine (D) positions. For example, the tRNA may have a dihydrouridine at one or more of positions U16, U17, U20, and U20b. In some embodiments the transfer RNA may have at least one uridine in its D loop, and in such embodiments the present methods may further comprise converting the uridine to dihydrouridine prior to replacing the uracil component with the fluorophore. Thus, the present methods may be used to label synthetic tRNAs (for example, tRNA transcripts) and introducing D residues into these tRNAs with a dihydrouridine synthase. Exemplary dihydrouridine synthases include, among others, Dus1p, Dus2p, Dus4p, and homologs or variants thereof. In one embodiment, the dihydrouridine synthase Dus1p may be used to convert a uridine at position U16 and/or position U17 of a tRNA. In another example, the dihydrouridine synthase Dus2p may be used to convert a uridine at position U20 of a tRNA. In yet another embodiment, the dihydrouridine synthase Dus4p may be used to convert a uridine at position U20 and/or position U20b of a tRNA.

Using the unmodified transcript of *E. coli* tRNA$^{Pro}$ as an example, which has U17 and U17a in the D loop, the present methods show that Dus1p catalyzes conversion of one of these uridines (mostly U17a) to D, and that the modified tRNA can be labeled with the fluorophores proflavin and rhodamine 110, with overall labeling yields comparable to those obtained with the native yeast tRNA$^{Phe}$. This method permits fluorescent labeling of, among other transcription components, in vitro synthesized tRNA transcripts, which can contain mutations not found in nature. Such labeled tRNAs have broad utility in research that involves studies of tRNA maturation, aminoacylation, and tRNA-ribosome interactions.

Labeling of a tRNA on one or more D positions may proceed in two steps (FIG. 1): first, reduction and opening of the heterocyclic uracil ring of dihydrouridine (for example, using sodium borohydride); then, replacing the base with a fluorophore bearing a primary amino group. The dihydrouridine may be reductively cleaved to form a leaving group, which may be replaced by the fluorophore. The leaving group may be 3-ureidopropanol.

The fluorophore with which the tRNA is labeled may be a rhodamine fluorophore. Suitable rhodamine fluorophores include rhodamine 110, rhodamine 123, rhodamine 6G, rhodamine B, and rhodamine 575, and those skilled in the art can readily identify additional rhodamine fluorophores for use in connection with the present methods. The rhodamine fluorophore may have a substituted secondary amine group.

Hydrazides are also good candidates for labeling of the tRNA. Moreover, reaction may proceed via a ribose present as an aldehyde, raising the possibility of hydrazone formation (FIG. 1). There are rich supplies of commercially available dyes linked to a hydrazide group, such as cy3-hydrazide and cy5-hydrazides (FIGS. 1A and 1B), many of which are designed for FRET or single molecule studies. Exemplary hydrazide fluorophores include Cy3 hydrazide, Cy3.5 hydrazide, Cy5 hydrazide, Cy5.5 hydrazide, Alexa Fluor 488 hydrazide, Alexa Fluor 555 hydrazide, Alexa Fluor 568 hydrazide, Alexa Fluor 594 hydrazide, and Alexa Fluor 647 hydrazide, Texas Red hydrazide, Lucifer yellow hydrazide, C5-DMB-ceramide, $C_6$-phosphatidylinositol 5-phosphate, Cascade Blue hydrazide, and ATTO dye.

The instant methods may further comprise "charging" or loading onto the 3' end of the tRNA an amino acid corresponding to a triplet nucleotide sequence that base-pairs to the anticodon sequence of the tRNA. The loading of the amino acid onto the 3' end of the amino acid may be performed in vitro using known techniques (see, e.g., Examples 6 & 8, infra). Alternatively or additionally, the tRNA may be subjected to conditions that are effective to load the amino acid onto the 3' end; for example, the tRNA may be introduced into the cellular environment where the necessary covalent linkage is catalyzed by an aminoacyl tRNA synthetase.

Also provided are nucleic acid compositions comprising a transfer RNA molecule including a fluorophore substitution for the uracil component of a dihydrouridine in a D loop of the transfer RNA. The fluorophore that replaces the uracil component of the dihydrouridine may be in accordance with the preceding description.

Introduction of rhodamine dyes into tRNA via substitution for uracil components of dihydrouridine residues in the D-loop of tRNA has numerous advantages. Nonlimiting advantages include: (1) Substitution proceeds with good retention of tRNA activity in protein synthesis; (2) A general way of labeling tRNA molecules, most or all of which have dihydrouridine residues in the D-loop is provided; (3) Rhodamines have rather low quantum yields for photobleaching and are thus suitable for single molecule studies which utilize rather high light intensities.

Introduction of Rhodamine 110 into tRNAs containing dihydrouridine residues may follow a preparation of tRNA$^{Phe}$ (rhod16/17) in accordance with the present invention. In addition, rhodamine-labeled tRNAs may be prepared having different fluorescence properties from those containing Rhodamine 110, in order to be able to distinguish between different tRNAs interacting with the ribosome during the course of a polypeptide synthesis. For this purpose, rhodamines (RDs) may be utilized, which, like RD 110, contain primary or secondary amines symmetrically placed at the 3- and 9-positions, allowing facile substitution for the dihydroU residues. As demonstrated by Lee (1997), substitution on either the xanthylium or phenyl rings changes both the maxima and broadness of fluorescence emission of rhodamines. A number of commercial rhodamines are available that are potentially suitable for this purpose, including Rhodamines 110 and 123 from Invitrogen (Carlsbad, Calif.), and Rhodamine 6G (Basic Red 1) from TCI America (Portland, Oreg.), which have emission maxima of 521 nm, 535 nm and 560 nm, respectively. Some exemplary rhodamine structures are illustrated below. If further spectral variants are needed, it will be possible to prepare other rhodamine derivatives, since their syntheses are straightforward using appropriately substituted phthalic anhydrides and aminophenols, as shown in with respect to the synthesis of rhodamine 575 (Scala-Valero, 1991).

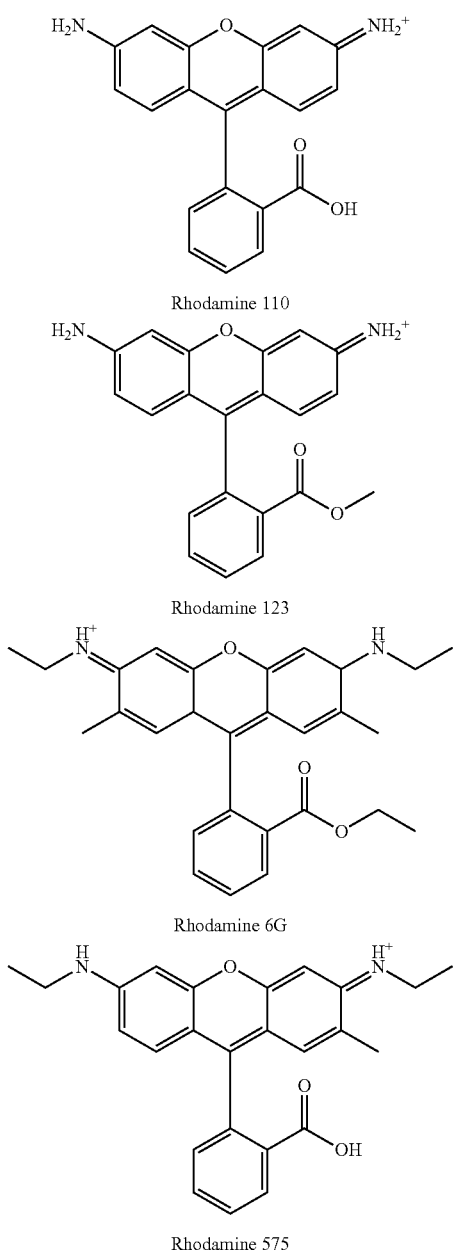

Rhodamine 110

Rhodamine 123

Rhodamine 6G

Rhodamine 575

Blanchard et al. (2004a,b) have employed different strategies for introducing fluorescence into tRNA in single molecule FRET studies of tRNA:tRNA interaction on the ribosome, with the most generally useful one for the present application being the alkylation of the 8-$s^4$U nucleotide (e.g., with a Cy3 maleimide) that is found in many tRNAs. However, in preliminary experiments, it was found that alkylation of tRNA$^{Phe}$ $s^4$U with a fluorophore gave a derivative which was considerably less active in polypeptide synthesis than either underivatized tRNA$^{Phe}$ or tRNA$^{Phe}$ (rhod16/17), making its use for this application disadvantageous. Nevertheless, given the ease of the alkylation reaction, the effects will be tested on polypeptide synthesis rates of alkylating other 8-$s^4$U containing tRNAs, to see whether derivatives prepared in this manner can be useful for the present studies.

In another aspect, the present invention provides methods for the assessment of protein synthesis in a translation system. Advantageously, such assessment may occur in real time, providing, inter alia, direct information about the dynamics of protein expression, and can be used to study dynamic patterns of protein synthesis in vitro or in vivo. The present methods for assessing protein synthesis in a translation system comprise providing a tRNA having a fluorophore substitution for the uracil component of a dihydrouridine in a D loop of the tRNA; introducing the labeled tRNA into the translation system; irradiating the translation system with electromagnetic radiation, thereby generating a fluorescence signal from the fluorophore; detecting the fluorescence signal; and, correlating the fluorescence signal to one or more characteristics of the protein synthesis in the translation system. The present methods are useful in single molecule as well as in ensemble settings.

The fluorescently labeled tRNA may be prepared in accordance with the methods described herein. Labeled tRNAs may include an entire complement of tRNAs extant in a particular cell type, organism type, or organelle type (such as mitochondria or chloroplast), or may include a subset of tRNAs, such as some or all tRNAs that are cognate of a specific amino acid, or a single type of isoaccepting tRNA that may be specific for one, two, or three different codons.

The translation system may comprise a cell-free (in vitro) system. Alternatively, the translation system may comprise a living cell. The introduction of a labeled tRNA into the translation system will accord with the type of translation system in use; for example, if the translation system comprises a living cell, the introduction of the labeled tRNA may comprise introducing the tRNA into the cellular environment. Those skilled in the art will readily appreciate appropriate techniques for introducing a tRNA into a living cell. For example, Sako et al. (2006) disclose a method for PTC suppression comprising introducing labeled suppressor tRNA into living cell thereby reading through PTC-containing mRNAS. Sako et al. show that introducing suppressor tRNA to cells possessing a frameshift mutation, induced the upregulation of the corresponding mRNA and accumulation of the resulting protein.

The present methods may further comprise providing at least one additional fluorescently labeled translation component. For example, the additional fluorescently labeled translation component may be a ribosome, a ribosomal protein, an initiation factor, an elongation factor, a messenger RNA, or a ribosomal RNA. The fluorophore with which a translation component is labeled may be a FRET partner (i.e., one member of a FRET pair that comprises a FRET donor and a FRET acceptor) with the fluorophore with which the tRNA is labeled, such that the detection of the fluorescence signal may comprise detecting energy transfer between the fluorophore of the translation component and the fluorophore of the tRNA.

Puglisi et al (U.S. Pat. No. 7,296,532) propose to use ribosomes, bound to a solid substrate through a specific attachment site, using labeled tRNAs as a FRET pair with another labeled component of the ribosome complex (usually a ribosomal protein), and using this labeled, cell-free translation system to monitor conformational dynamics and translation rates. For such techniques, the labeling methods for tRNAs disclosed herein are of particular use.

The irradiation of the translation system will also depend in part on the type of translation system in use. For example, if the translation system comprises a cell-free system, the irradiation may comprise exposing all or part of the in vitro setting to the electromagnetic radiation. If the translation system comprises a living cell (which may be a population of living cells), the irradiation may comprise exposing a single cell, a desired subset of cells, or an entire population of cells to the electromagnetic radiation. The electromagnetic radiation may take any appropriate form. For example, the electromagnetic radiation may comprise a wavelength of light that is sufficient to induce fluorescence of the fluorophore with which the tRNA is labeled, a fluorophore with which at least one additional component of the translation system is labeled, or both (i.e., the electromagnetic radiation may comprise one or more different wavelengths, frequencies, intensities) In one example, where a FRET system is intended, the electromagnetic radiation may be a laser light source that is sufficient to excite the fluorophore with which the tRNA is labeled such that it may function as a donor fluorophore and thereby emit energy sufficient to excite one or more accepting fluorophore that is bound to one or more respective components of the translation system. Depending on the type of fluorophore with which the tRNA is labeled, and, where applicable, the type of fluorophore with which at least one additional component of the translation system is labeled, as well as other factors such as the opacity of the translation system, the electromagnetic radiation may comprise one or more specific wavelengths, frequencies, or intensities, and may be applied for an appropriate duration, in accordance with various factors that those skilled in the art will readily appreciate.

The irradiation of the translation system directly or indirectly results in the generation of a fluorescence signal from the fluorophore with which the tRNA is labeled. In accordance with the present invention, the fluorescence signal is detected using an appropriate means. Detection means may include the use of one or more of photodiodes, phototransistors, photomultipliers, charge-coupled device cameras, or any other appropriate device or arrangement of devices. The signal may correspond to simple fluorescence, FRET, lifetime, or anisotropy, and relate to the frequency, sequence, intensity, or any other relevant parameter of the detected fluorescence and/or its relationship to other events occurring in the translation system—whether protein synthesis activity other aspect of the state of a translation system—as will be discussed more fully herein.

The conversion of the detected signal to data and the interpretation of the data may be performed using any appropriate devices and techniques; those skilled in the art will be familiar with numerous suitable devices and techniques. The fluorescence signal may therefore be correlated to one or more characteristics of the protein synthesis that occurs within the translation system. Characterization of real time protein synthesis represents a fundamental advance in the efforts to understand both normal and abnormal cellular processes. Protein synthesis monitoring (PSM), a technique with which those skilled in the art will be familiar, utilizes a fluorescent labeling scheme for tRNAs and ribosomes to produce optical signals for identifying the synthesized proteins. PSM may be used to monitor thousands of labeled ribosomes simultaneously, recording, analyzing and comparing patterns of protein synthesis in a variety of live cells and tissues, which can be repeated over hours and days. See, e.g., PCT Application WO 2005/116252. In one example, a cell-free, prokaryotic polypeptide translation system is labeled, the signals produced captured and analyzed, and the polypeptides being synthesized is identified. The methods for in vitro protein synthesis advance the technology to full-length proteins, and to observations in live cells. The methods for labeling tRNA utilized in PSM may result in applications in drug discovery and diagnostics. Other exemplary characterization parameters and general techniques may be found in U.S. Pat. No. 7,296,532 to Puglisi, et al., and the present methods for assessing protein synthesis are fully applicable and adaptable to the uses described in that patent.

Fluorescence resonance energy transfer (FRET) occurs between two neighboring fluorophores when the emission spectrum of one (the donor) overlaps the excitation spectrum of the second (the acceptor). FRET is mediated by dipole-dipole interactions, where the excitation energy absorbed by the donor is transferred to the acceptor. The result of this exchange of energy is seen as a decrease in the specific emission intensity of the donor and an increase in the specific emission intensity of the acceptor.

The drive for increased throughput within the drug discovery process has prompted a new phase of assay development combining miniaturisation with automation. In parallel, there has also been a concerted effort to shift from conventional radiometric detection technologies to those based around fluorescence. The technique of FRET provides a non-radiometric route for the detection of numerous biological interactions in homogenous assay formats. FRET describes the transfer of excitation energy from a donor fluorophore to an acceptor chromophore when the two dye molecules are separated by <100 Å and overlap occurs between the donor emission, and acceptor absorption spectra. Pursuant to the present invention, protein-DNA and protein-peptide binding events have been examined using FRET combined with fluorescent imaging.

In one exemplary embodiment of the present methods of assessing protein synthesis, the at least one additional fluorescently labeled translation component may comprise a ribosome, wherein the introduction of said labeled tRNA into the translation system contacts the labeled tRNA with the fluorescently labeled ribosome, and the method further comprises detecting a timed sequence of Fluorescence Resonance Energy Transfer (FRET) signals characteristic of one or more polypeptides synthesized by the ribosome in order to identify at least one of the polypeptides. In another aspect, the present methods may involve the direct monitoring of the movements of tRNA or tRNA mutants on the ribosome. One exemplary method for measuring protein synthesis in vitro or in vivo from one or more living cells involves the production of a transient FRET signal when a specific tRNA is processed by the ribosome. For example, the technique may involve a) the preparation of E. coli ribosomes incorporating a fluorescent label in protein L11, which is proximal to the entry (A-site) of tRNA binding to the ribosome and/or in protein L1, which is proximal to the tRNA exit (E-site) of the ribosome, and b) the preparation of fully functional fluorophore-substituted tRNAs, e.g., a rhodamine labeled tRNA, which are capable of acting as FRET donors or acceptors when bound in the A or E-sites of appropriate fluorescent-labeled ribosomes.

Proflavin-substituted tRNA$^{Phe}$, tRNA$^{Phe}$(prf 16/17), prepared via reduction of dihydroUs at positions 16 and 17 with NaBH$_4$ and replacement of the resulting ureidopropanol with proflavin (Wintermeyer, 1979), has been used in stopped-flow studies of tRNA interaction with the ribosome (Pape, 1998). As proflavin is not a suitable chromophore for single molecule studies, proflavin was substituted by rhodamine 110, which has acceptable brightness and stability for single molecule studies. tRNA$^{Phe}$ (rhod16/17) derivative is fully functional, both as an acceptor of Phe in the PheRS-catalyzed charging reaction and in poly(U)dependent poly(Phe) synthesis. This tRNA derivative has a fluorescence maximum at 530 nm on excitation at 497 nm, making it a suitable donor in FRET studies with Cy3 as acceptor (Forster R$_0$ of ~67 Å). In ongoing stopped-flow work, a FRET signal was detected when the ternary complex EF-Tu.GTP-PhetRNA$^{Phe}$(rhod16/17) binds to ribosomes labeled with Cy3-L11 which are programmed with mRNA022 and contain fMet-tRNA$^{fmet}$ in the P-site and an empty UUU-programmed A-site. The FRET signal has maximal intensity on initial binding of the ternary complex to the A/T site of the ribosome and GTP hydrolysis, and decreases in intensity as inorganic phosphate ($P_i$) and EF-Tu.GDP are released and Phe-tRNA$^{Phe}$ is accommodated into the A-site. The $t_{1/2}$ for this decrease is ~250 ms. When the reaction is performed in the presence of kirromycin (Kir), an antibiotic which allows ternary complex binding and GTP hydrolysis but inhibits $P_i$ and EF-Tu.GDP release, the initial higher FRET state is maintained. This result demonstrates that a clear FRET signal is observed on entry of a charged tRNA into the ribosomal A-site.

EXEMPLARY EMBODIMENTS

Example 1

Specific Introduction of a D Residue Into an *E. coli* tRNAPro/UGG Transcript by Yeast Dus1p The present methods use the yeast enzyme Dus1p (Xing et al., 2004), expressed in *E. coli* as a His-tag fusion, to introduce a D residue into an in vitro tRNA transcript. Dus1p catalyzes U→D conversion specifically at positions 16 and 17 of tRNAs, utilizing FAD as a cofactor and NADH and NADPH as electron donors (Xing et al., 2004). Because virtually all tRNA genes in databases encode U16, U17, or both, this approach allows introduction of D residues at these positions, thus creating potential sites for fluorescent labeling. The heterocyclic ring of D is subject to reductive cleavage by sodium borohydride, yielding 3-ureidopropanol bound to the ribose C-1' position (Cerutti & Miller, 1967), which is a facile leaving group that is readily replaced by fluorophores bearing a primary amino group (Wintermeyer & Zachau, 1974). Second, it is herein demonstrated that rhodamine 110, a photobleaching-resistant fluorophore commonly used in single-molecule studies, which also has a stronger emission intensity than the dyes used by Wintermeyer and Zachau (1974), is competent for such replacement, generating a fluorescent-labeled tRNA that is active in protein synthesis The transcript of *E. coli* tRNA$^{Pro/UGG}$, prepared by in vitro run-off transcription and containing U residues at positions 17, 17a, and 20, was subjected to modification by Dus1p. The amount of U→D conversion was determined by a previously established colorimetric method (Jacobson & Hedgcoth, 1970) which measures the amount of acyclic ureido group formed by alkaline cleavage of the D ring. Calibration of the assay with dihydrouracil reveals a linear relationship between absorption and concentration of ureido group. Application of this assay to bulk tRNA isolated from *E. coli* yields an average number of D per *E. coli* tRNA of 1.5±0.5 (Table 1), similar to the previously determined value of 1.4±0.1 (Jacobson & Hedgcoth, 1970). The number of D residues per transcript of *E. coli* tRNA$^{Pro/UGG}$ modified with Dus1p (2.7 μM), determined over a range of transcript concentrations (16-40 μM), was 0.97±0.01 (Table 1, below), indicating that only one of the three U residues at 17, 17a, and 20 was converted to D.

TABLE 1

Number of D residues per tRNA

| | tRNA (μM) | OD$_{550}$ | D Content (μM) | D/tRNA | D/tRNA Average |
|---|---|---|---|---|---|
| *E. coli* tRNA$^{Pro/UGG}$ | 0 | 0 | 0 | 0 | 0.97 ± 0.2 |
| | 16 | 0.10 | 15.3 | 0.96 | |
| | 24 | 0.19 | 27.5 | 1.15 | |
| | 32 | 0.20 | 30.0 | 0.94 | |
| | 40 | 0.23 | 33.5 | 0.84 | |
| *E. coli* total tRNA | 0 | 0 | 0 | 0 | 1.5 ± 0.5 |
| | 8 | 0.12 | 17.5 | 2.2 | |
| | 16 | 0.17 | 25 | 1.6 | |
| | 32 | 0.27 | 39 | 1.2 | |
| | 40 | 0.32 | 47 | 1.2 | |

To map the site of modification within the transcript, D was converted to a ureido group, which blocks primer extension (Xing et al., 2004). An oligonucleotide primer was designed to complement G42 to G22 in *E. coli* tRNA$^{Pro/UGG}$ and the products of primer extension were analyzed by denaturing polyacrylamide gel electrophoresis (PAGE). This analysis identifies position G18 in the Dus1p-modified transcript as a major stop site, not seen with the unmodified transcript, indicating that the U→D modification catalyzed by Dus1p occurs at U17a, rather than at U17. Although the mechanism of how Dus1p recognizes tRNA is unknown at the present, the demonstrated specificity at U17a, which is immediately adjacent to the conserved G18-G19 sequence common to all tRNA species, suggests that this enzyme may recognize G18-G19 as the determinant for modification. The product of Dus1p modification is denoted as *E. coli* tRNA$^{Pro/UGG}$(D-17a).

Example 2

Rhodamine Labeling of D-Containing tRNAs

In vitro transcribed *E. coli* tRNA$^{Pro/UGG}$(D-17a) was labeled with either proflavin or rhodamine 110, using standard reductive cleavage conditions (leading to incorporation values of 1.0 and ~0.5, respectively, and giving rise to labeled tRNAs denoted tRNA$^{Pro}$(prf) and tRNA$^{Pro}$(rhd), respectively. Labeling stoichiometries were determined from the ratio of absorption in the visible (462 nm for proflavin, 512 nm for rhodamine 110) to that at 260 nm for tRNA (corrected for a contribution from the dye). The lower stoichiometry in the case of rhodamine may be due to its expected lower nucleophilicity as compared with proflavin, given its much lower pKa value [rhodamine 110, 4.3 (Boonacker & Van Noorden, 2001); proflavin, 9.6 (Horobin et al., 2006)] and its somewhat more hindered primary amine. Similarly, labeling of native yeast tRNA$^{Phe}$, which contains D residues at positions 16 and 17, under the same conditions led to incorporation values of 2.0 and 1.0 for proflavin or rhodamine 110, respectively, and giving rise to labeled tRNAs denoted tRNA$^{Phe}$(prf) and tRNA$^{Phe}$(rhd), respectively.

Example 3

Biochemical Characterization of Fluorescent-Labeled tRNAs tRNA$^{Pro}$(prf), tRNA$^{Phe}$(prf) and tRNA$^{Phe}$(rhd) are each good substrates for their respective synthetases, with ~75% efficiency of aminoacylation of tRNA$^{Pro}$(prf) as compared with the unlabeled transcript (900 pmol/A$_{260}$ versus 1200 pmol/A260), and 85% and 77% of aminoacylation of tRNA$^{Phe}$(prf) (1100 pmol/A$_{260}$) and tRNA$^{Phe}$(rhd) (1000 pmol/A$_{260}$), respectively, as compared to the unlabeled tRNA$^{Phe}$ (1300 pmol/A$_{260}$). The results with tRNA$^{Phe}$(prf) parallel those reported earlier (Wintermeyer & Zachau, 1979).

In contrast, aminoacylation of purified tRNA$^{Pro}$(rhd) gave quite low Pro incorporation, ~10% as compared with the unlabeled transcript. Here the labeled transcript was purified away from unlabeled transcript by a recently developed method (Hou et al., 2006) in which oligonucleotide complementary to the site of the label is hybridized to the unmodified transcript. Since labeled transcript is inaccessible to such hybridization, subsequent RNase H digestion allows selective removal of unmodified transcript. The ~10% level of aminoacylation activity suggests that ProRS is inhibited by the presence of the bulkier rhodamine group in the tRNA tertiary core to a much greater extent than when the tRNA is proflavin-labeled. These results are consistent with a previous finding that this enzyme is sensitive to structural alterations in the core (Liu & Musier-Forsyth, 1994) and support the notion that the structure of the tRNA tertiary core is a determinant for aminoacylation by ProRS. Thus, while PheRS can easily accommodate rhodamine in the tRNA tertiary core, ProRS cannot. The contrast between these two enzymes illustrates the idiosyncratic nature of aminoacyl-tRNA synthetases with respect to their sensitivity to the structure of the tRNA tertiary core.

Phe-tRNA$^{Phe}$(rhd) was also tested for its ability to participate in ribosome-catalyzed poly(U)-dependent poly(Phe) synthesis, giving rates and extents of reaction similar to those obtained with unlabeled Phe-tRNA$^{Phe}$.

Example 4

Fluorescent Labeling of tRNA Utilizing Dus Enzymes to Introduce D Residues into a tRNA Transcript A general method is provided for fluorescent labeling of tRNA that utilizes one of the Dus enzymes to introduce D residues into a tRNA transcript and subsequently replaces the D residues with a primary amine-containing fluorophore such as proflavin or rhodamine 110. The method is general for tRNA species, because all but a small number of tRNAs have U residues in the D loop that are substrates for the Dus enzymes (Sprinzl et al., 1998). Even in the rare cases where U is absent from a tRNA (e.g. *Steptomyces lividans* tRNA$^{Cys}$), it may be possible to introduce a U into the D loop by site-directed mutagenesis, either as a replacement or as an insertion, as long as the introduced U does not alter the normal functions of the tRNA. Here the focus was on yeast Dus1p, which is specific for U16 and U17. Other yeast enzymes are specific for U20 (Dus2p) and for U20 and U20b (Dus4p) (Xing et al., 2004). Although not as fully characterized, *E. coli* also encodes several Dus enzymes (Bishop et al., 2002), which offer additional options for introducing D residues. Thus, the potential to use the described method for fluorescent labeling of tRNA is virtually unlimited.

The present labeling methods should prove useful in a wide variety of research involving tRNAs. One immediate application is to use the methods to directly monitor the dynamic interaction of mutant tRNAs with the ribosome (Pan et al., 2006; Pan et al., 2007), but other tRNA-enzyme reactions are amenable to this approach as well. Since tRNA$^{Pro}$(prf), tRNA$^{Phe}$(prf) and tRNA$^{Phe}$(rhd) are good substrates for their respective synthetases, such labeled tRNAs can be used to yield insights into tRNA conformational rearrangements upon interaction with its cognate tRNA synthetase. Also, because eukaryotic tRNAs are believed to be channeled through a multi-synthetase complex (Negrutskii & Deutscher, 1991), the technique may be used to study the dynamics of the multi-synthetase complex assembly. Other possibilities include enzymatic reactions that occur during maturation of tRNA, such as 5' processing, intron splicing, anticodon modification, and CCA end addition. Finally, the described method will be also useful for studying the kinetics and thermodynamics of tRNA folding, which provides the basis for understanding the folding of larger RNA molecules such as ribozymes.

Example 5

Replacement of D Residues with Cy-Hydrazides

Yeast tRNA$^{Phe}$ has D residues at positions 16 and 17. Labeling of yeast tRNA$^{Phe}$ with Cy3 hydrazide was initially attempted by using the two-step procedure previously employed to label the D positions with proflavin or rhodamine 110 (Wintermeyer and Zachau, 1979; Betteridge, 2007), in which reduction of the D residue by treatment with NaBH$_4$ at neutral pH and room temperature is followed by reaction with 2 mM dye at pH 3, 37° C. for 45' to 90'. However, utilization of these conditions led to very poor incorporation of dye (<0.05 Cy3/tRNA as compared with essentially stoichiometric incorporation of proflavin (1.7-2.0 prf/tRNA (Pan, 2007)) and considerably higher incorporation of rhodamine 110 (1.0/tRNA (Betteridge, 2007)).

Figure 2:
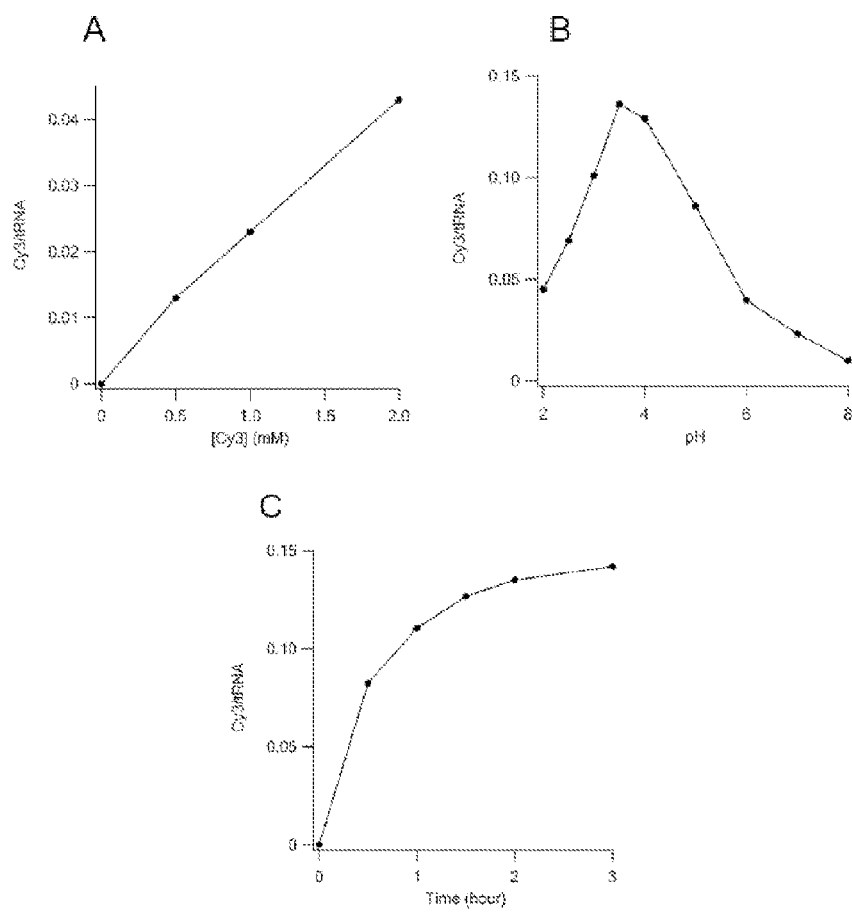
FIG. 2 provides data pertaining to the optimization of the conditions for the labelling of tRNAs.

A systematic study of dye uptake as a function of pH and time of incubation (FIG. 2) was undertaken. In each reaction in (FIG. 2A-C) 200 pmol of NaBH$_4$-treated tRNA$^{Phe}$ was mixed with Cy3 in 100 µl of 0.1 M either Na formate (pH<4), Na acetate (pH 4 and 5), or Na phosphate buffer (pH≥6). After the reaction pH was brought up to 7.5 to stop the reaction, and phenol extractions and ethanol precipitations were performed to remove excess dyes before OD measurements. FIG. 2A relates to dye concentration dependence: pH=3.0, incubation time 1 hr, temperature 37° C. FIG. 2B relates to pH dependence: [Cy3]=4 mM, temperature 37° C., incubation time 2 hr. FIG. 2C relates to time dependence. [Cy3]=4 mM, temperature 37° C., pH 3.7.

These studies led to the choice of pH 3.7 and 2 hrs as preferred. Under these conditions, dye incorporation increased linearly with dye concentration in the range 0.5 mM-4 mM, reaching 0.15 Cy3/tRNA at 4 mM. Further increasing Cy3 hydrazide concentration to 40 mM yielded an uptake of 1.2-1.3 Cy3/tRNA$^{Phe}$. Application of the high concentration procedure to other tRNAs and to substituting Cy5 hydrazide for Cy3 hydrazide afforded the following results: 0.94 Cy3/*E. coli* tRNA$^{arg}$ (2 D residues); 0.39 Cy5/*E. coli* tRNA$^{fMet}$ (1 D residue).

In addition to D residues, yeast tRNA$^{Phe}$ has a wybutine base at position 37. This base can be excised and replaced with primary amine nucleophiles attached to dyes by prolonged incubation at pH 2.9 without the need for NaBH$_4$ reduction, although the overall reaction was found to proceed more slowly than substitution at the D positions following NaBH$_4$ reduction (Thiebe and Zachau, 1968; Wintermeyer and Zachau, 1971; Wintermeyer and Zachau, 1979).

Figure 3:
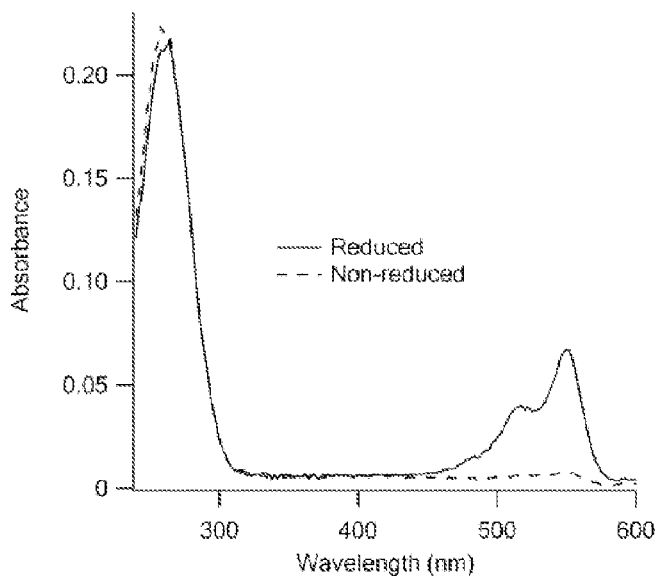
FIG. 3 provides the results of an experiment designed to compare fluorophore incorporation when a reduction step is omitted versus when such step is included.

To test whether substitution at position 37 was competitive with substitution at the D positions under the optimized conditions described above, a direct comparison of dye incorporation was made between when the NaBH$_4$ step is omitted versus when it is included (FIG. 3). 400 pmol of NaBH$_4$-treated or untreated tRNA$^{Phe}$ was labeled with Cy3 using the standard protocol (see Example 8, infra, Materials and Methods). Peaks at 260 and 550 nm corresponds to absorption of tRNA and Cy3, respectively.

Consistent with the earlier work, values of dye incorporation of ≤0.08 and 1.2 Cy3/tRNA, respectively, were obtained, demonstrating that virtually all of the dye is incorporated into the D positions.

Example 6

Optimization of the Charging of Cy3-Labeled Phe-tRNA$^{Phe}$

Synthesis of charged, Cy3-labeled tRNA$^{Phe}$ for use in functional studies may be considered to be a three-step procedure, involving NaBH$_4$ reduction, labeling with Cy3 hydrazide, and charging by Phe-RS. Since reduction must precede labeling, there are three options for how these steps are sequenced: 1) charging-reduction-labeling; 2) reduction-labeling-charging; or 3) reduction-charging-labeling. Option 1) was found to yield poor results, because of the high lability of Phe-tRNA$^{Phe}$ toward NaBH$_4$ treatment, which in our hands results in a 90% loss of Phe from the tRNA. Option 2) was also found to be non-optimal, because Cy3-labeled tRNA$^{Phe}$ is less efficiently charged by Phe-RS under standard conditions than unlabeled tRNAPhe. For example, tRNA$^{Phe}$ containing 1.3 Cy3s charges to a level of 480 pmol Phe/A$_{260}$, approximately 2-fold lower than the level of ~900 pmol Phe/A$_{260}$ obtained with unlabeled tRNA$^{Phe}$.

Figure 4:
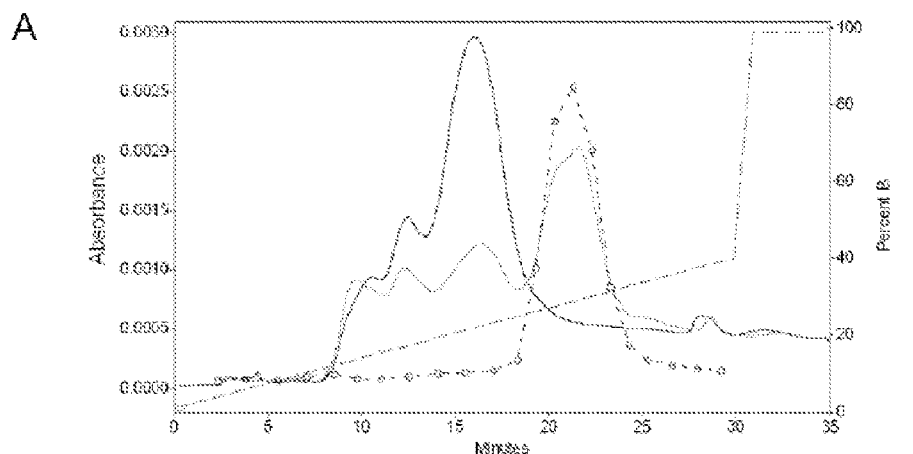
FIG. 4 shows data derived from studies pertaining to the purification of amino acid-charged, fluorophore-labeled tRNA.
Figure 4:
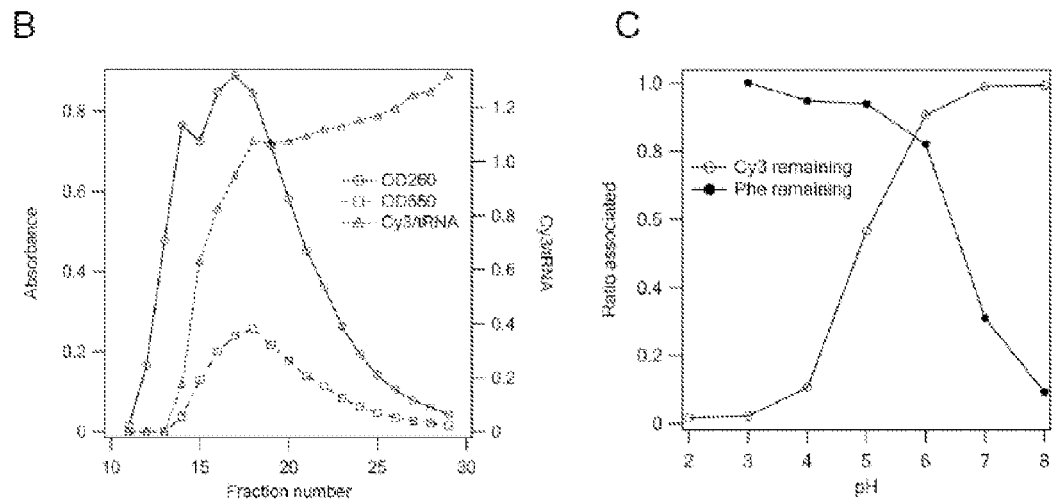

The best results were obtained with option 3. FIG. 4A depicts the results of purification of Phe-tRNAPhe that was charged after NaBH$_4$ treatment using a reverse-phase column on HPLC. FIG. 4B depicts the results of purification of Cy3-Phe-tRNA$^{Phe}$ using a Mono-Q column on FPLC. In the preferred procedure, shown in FIG. 4A, the reduction and charging steps were followed by RP-HPLC to separate charged from uncharged material (FIG. 4A), and the charged fraction was labeled with 40 mM Cy3 hydrazide at pH 3.7 as described above. The final material was subjected to FPLC (FIG. 4B), leading to a major fraction, denoted Phe-tRNA$^{Phe}$(Cy3), containing 1.0 Cy3/tRNA$^{Phe}$ and charged to a level of 1190 pmol Phe/A$_{260}$. Here the choice of pH 6.0 for the eluting buffer is preferred, since higher pH leads to loss of Phe, whereas lower pH leads to loss of Cy3. Similar FPLC of the Cy5-labeled fMet-tRNA$^{fMet}$ prepared as described above via option 2) and with no RP-HPLC purification resulted in partially purified material denoted fMet-tRNA$^{fMet}$(Cy5), containing 0.75 Cy5/tRNA$^{fMet}$ and charged to a level of 590 pmol fMet/A$_{260}$. FIG. 4C illustrates the retention of [$^3$H]-Phe and Cy3 with tRNA$^{Phe}$ following incubation of [$^3$H]-Phe-tRNA$^{Phe}$(Cy3) at 37° C. for 2 hr at various pH values. [$^3$H]-Phe was determined by TCA precipitation and counting. Cy3 was determined following ethanol precipitation. Buffers were the same as the study shown in FIG. 2B.

The observation that pH 3.7, which is preferred for reduced tRNA$^{Phe}$ labeling by Cy3 (FIG. 2B), would lead to unacceptable loses of Cy3 on isolation of Cy3-labeled tRNA$^{Phe}$ is readily explainable. Raising the concentration of hydrazide shifts the equilibrium shown in FIG. 1 in the direction of imine formation, consistent with our results, and the weakly acidic pH optimum for the rate of hydrazide adduct formation is in accord with results published for similar condensations (Jencks, 1964). On the other hand, isolation of Cy3-labeled tRNA is carried out under conditions in which hydrolysis of the hydrazide adduct is essentially irreversible, mandating the use of a higher pH to kinetically trap the adduct, the hydrolysis of which is also acid-catalyzed.

Example 7

Functional Assays

Formation of 30S Initiation Complex (30SIC).

Figure 5:
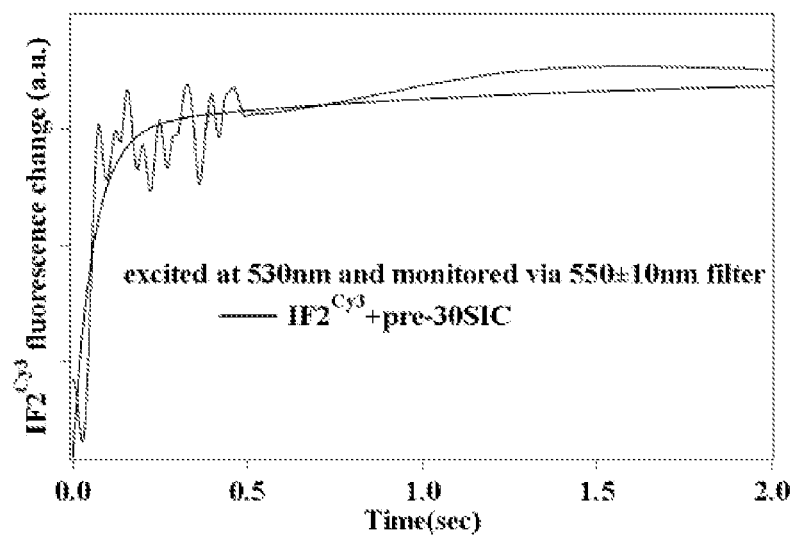
FIG. 5 shows the results of time course studies of the rate of formation of the 30S initiation complex using labelled tRNA in accordance with the present invention.
Figure 5:
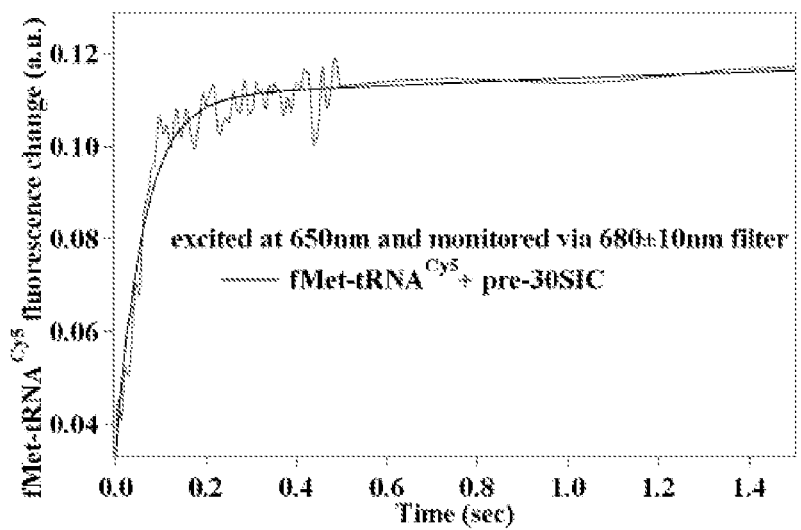

Previous studies have shown that the rate of 30SIC formation can be monitored by changes in fluorescence, using either a proflavin derivative of fMet-tRNA$^{fMet}$ [fMet-tRNA$^{fMet}$(prf)] (Grigoriadou, 2007a) or a coumarin (Grigoriadou, 2007a) or Cy3 (Qin, 2008) derivative of IF2. Here, stopped-flow fluorescence measurements using limiting amounts of either IF2$^{Cy3}$ (prepared as described: Qin et al., in preparation) or fMet-tRNA$^{fMet}$(Cy5), were carried out with 0.3 μM 30S subunits at 20° C., essentially as described (Grigoriadou et al., 2007b). Using fMet-tRNA$^{fMet}$(Cy5) a rate of 30SIC formation that was essentially the same as that measured from Cy3-IF2 (FIG. 5) was obtained, suggesting that Cy5-fMet-tRNA$^{fMet}$ is fully functional in formation of 30SIC. FIG. 5A shows the fluorescence change of Cy3-IF2. The trace was fit to a single exponential term with a rate of 21±2 s$^{-1}$, and a slope term. FIG. 5B shows the fluorescence change of Cy5-fMet-tRNA$^{fMet}$. The trace was fit to a single exponential term with a rate of 19±1 s$^{-1}$, and a slope term. Excitation was at 530 nm or 650 nm and fluorescence was monitored through a bandpass filter (550±10 nm or 680±10 nm) for IF2$^{Cy3}$ or fMet-tRNA$^{fMet}$(Cy5), respectively.

Formation and Translocation of a Pre-Translocation (PRE) Complex.

Three samples of PRE complex made with mRNA-MFK programmed ribosomes were formed in parallel, by addition of: i) both fMet-tRNA$^{fMet}$(Cy5) and Phe-tRNA$^{Phe}$(Cy3) (the donor-acceptor or DA sample); ii) unlabeled fMet-tRNA$^{fMet}$ and Phe-tRNA$^{Phe}$(Cy3) (the donor alone or DU sample); and iii) fMet-tRNA$^{fMet}$(Cy5) and unlabeled Phe-tRNA$^{Phe}$ (the acceptor alone or UA sample). These complexes resulted in fMetPhe formation, and were purified by ultracentrifugation through a sucrose cushion prior to their utilization in the fluorescence measurements described below. The stoichiometries of fMetPhe formed, and of [$^3$H]-Phe and [$^{35}$S]-fMet cosedimenting with the ribosome (see Table 2, below), are very similar whether using Cy3-labeled or unlabeled Phe-tRNA$^{Phe}$ (DU and DA samples vs. UA sample) or Cy5-labeled or unlabeled fMet-tRNA$^{fMet}$ (UA and DA samples vs. DU sample), providing a convincing demonstration of the functionality of the Cy-labeled tRNAs in binding to the ribosome and participating in dipeptide formation, as part of PRE complex formation.

TABLE 2

Stoichiometry of complexes formed with labeled tRNAs

|  | fMet/ 70S | Phe/ 70S | Lys/ 70S | fMetPhe/ 70S | Cy5/ 70S | Cy3/ 70S | Rel. donor decrease |
|---|---|---|---|---|---|---|---|
| PRE (DU) | 0.71 ± 0.03 | 0.78 ± 0.06 | 0 | 0.55 ± 0.03 | 0 | 0.75 ± 0.02 | ND |
| PRE (UA) | 0.64 ± 0.05 | 0.63 ± 0.05 | 0 | 0.48 ± 0.04 | 0.63 ± 0.02 | 0 | ND |
| PRE (DA) | 0.74 ± 0.03 | 0.68 ± 0.04 | 0 | 0.54 ± 0.03 | 0.61 ± 0.04 | 0.71 ± 0.03 | 0.54 |
| POST (DA) | 0.62 ± 0.03 | 0.64 ± 0.04 | 0 | ND | 0.21 ± 0.02 | 0.70 ± 0.03 | 0.32 |
| POST2 (DA) | 0.63 ± 0.03 | 0.58 ± 0.04 | 0.57 ± 0.05 | ND | 0.13 ± 0.02 | 0.05 ± 0.02 | 0 |

Figure 6:
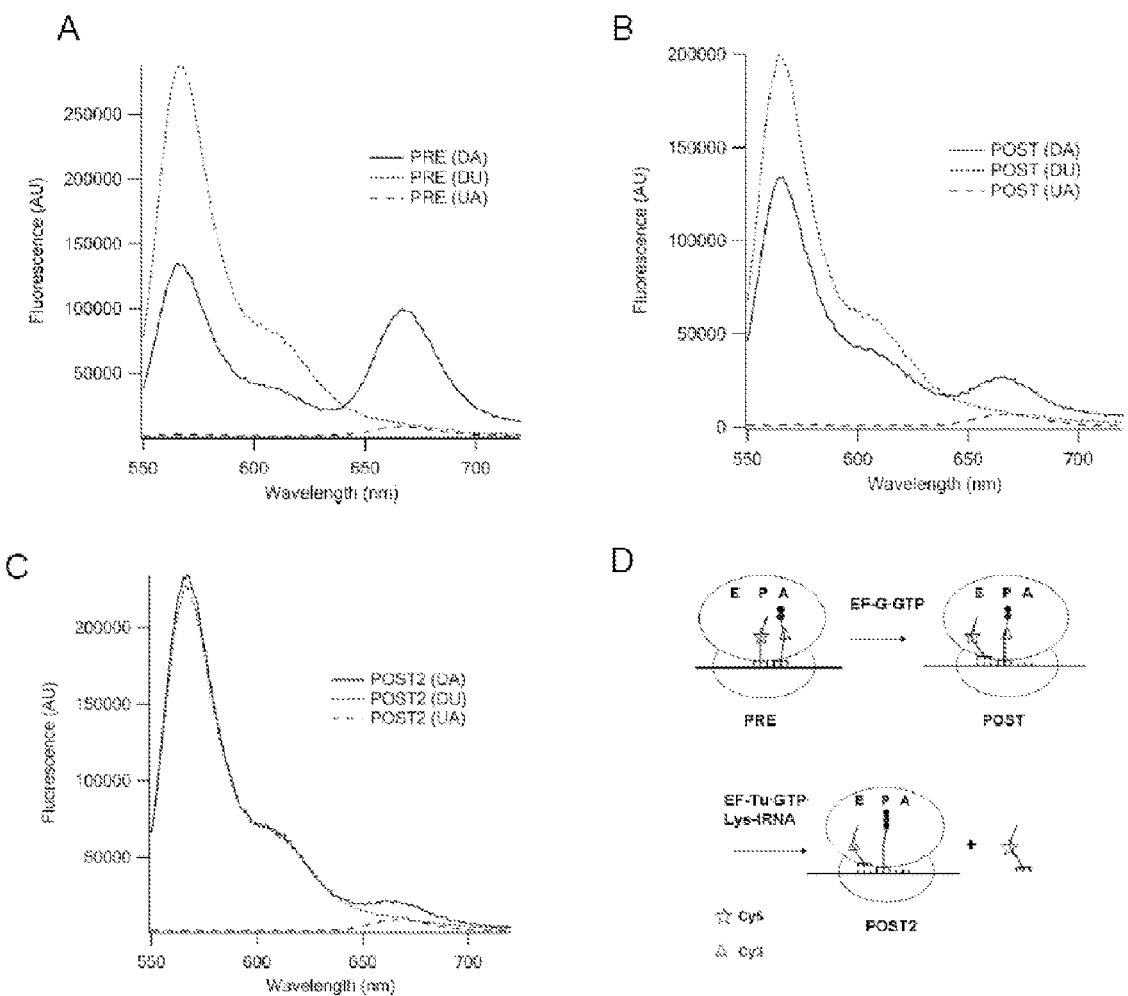
FIG. 6 provides fluorescence spectra of "PRE", "POST", and "POST2" complexes.

FIG. 6 shows the fluorescence spectra of PRE (FIG. 6A), POST (FIG. 6B), and POST2 (FIG. 6C) complexes. DA, Cy3-tRNAPhe+Cy5 tRNAfMet; DU, Cy3-tRNAPhe+unlabeled tRNAfMet; UA, unlabeled tRNAPhe+Cy5 tRNAfMet. Fluorescence spectra of the three PRE samples (FIG. 6) provide clear evidence of FRET in the DA sample, as shown by the increase in acceptor and decrease in donor fluorescent intensities relative to the A and D samples, respectively. Addition of EF-G.GTP to each of the samples leading to post-translocation (POST) complex formation results in a marked decrease in FRET efficiency, as evidenced by the decreases observed between the DA sample and both the UA and DU samples (FIG. 6; Table 2). This decrease in FRET efficiency is consistent with an increase of 14 Å in the distance between the dihydrouracil positions of tRNA$^{Phe}$ and tRNA$^{fMet}$, calculated from coordinates determined by X-ray crystallographic analysis of ribosome-bound tRNAs (Yusupov et al. 2001), as these two tRNAs move from occupying the A- and P-positions, respectively, in the PRE complex (28 Å apart), to occupying the P- and E-positions, respectively, in the POST complex (42 Å apart). Addition to the three PRE samples of both EF-G.GTP and the next cognate ternary complex, EF-Tu.GTP.Lys-tRNA$^{Lys}$ ternary complex reduces FRET efficiency to zero (FIG. 6C), consistent with the expected removal of tRNA$^{fMet}$ from the ribosome on A site binding and translocation of Lys-tRNA$^{Lys}$ to form the POST2 complex. FIG. 6D is a schematic showing transition from PRE to POST to POST2.

Figure 7:
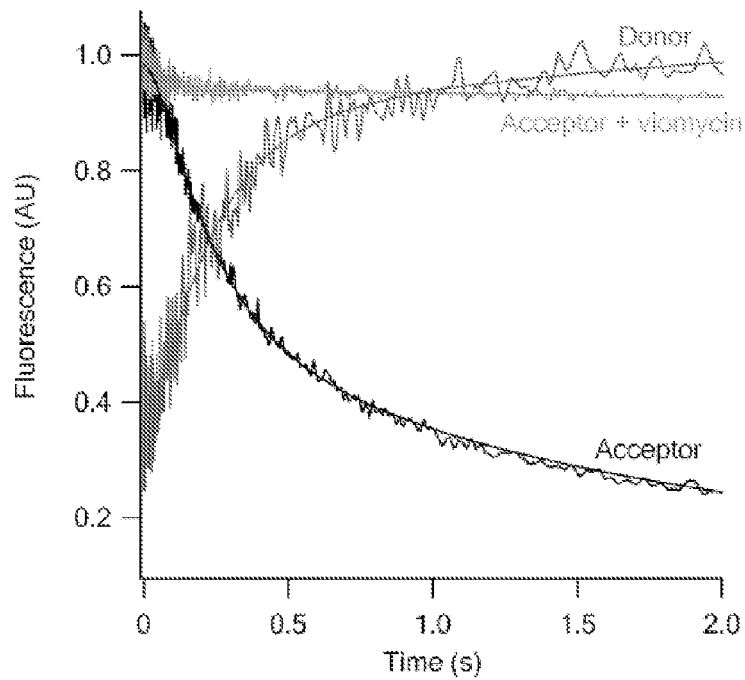
FIG. 7 shows the kinetics of FRET change during translocation to form the first POST complex on rapid mixing of EF-G.GTP with the PRE(DA), PRE(DU), or PRE(UA) complexes.

The kinetics of FRET change during translocation to form the first POST complex on rapid mixing of EF-G.GTP with the PRE(DA), PRE(DU), or PRE(UA) complexes are displayed in FIG. 7, in which "Acceptor"=monitored at acceptor wavelength (680±10 nm), and "Donor"=monitored at donor wavelength (570±10 nm). These are the corrected curves (see Example 8, infra, Materials and Methods). Global fitting of the data to a 3-step model gives the following rate constants: $k_1=22±4$ s$^{-1}$, $k_2=4.9±0.6$ s$^{-1}$, $k_3=0.57±0.06$ s$^{-1}$. "Acceptor+Viomycin"=in the presence of viomycin monitored at acceptor wavelength. Here, 100 uM of viomycin was preincubated with PRE for 1 min at 37° C. before mixing with EF-G.GTP. The small rapid decrease has a rate of 16±2 s$^{-1}$. The traces shown are corrected for contributions to fluorescence change from the donor alone and acceptor alone traces. For acceptor, the corrected trace is equal to DA−(DU+UA). For donor, the corrected trace is equal to (DA−UA)/DU. Both traces were globally fit to a 3-step model, A→B→C→D, in which the fluorescences of A and B are essentially equal, and the large change in FRET signal is associated with B to C conversion. The "Acceptor+Viomycin" trace measures the corrected acceptor fluorescence change when PRE complex was pre-incubated with viomycin (100 uM) for 1 min at 37° C. before mixing with EF-G.GTP.

The two rapid phases, corresponding to a lag in FRET efficiency change, followed by a large drop, proceed with apparent rate constants of 22±4 s$^{-1}$ and 4.9±0.6 s$^{-1}$ (a slower third phase, $k_{app}$ equal to 0.6±0.1 s$^{-1}$, occurs with a slight additional loss of FRET efficiency, reflecting slight additional tRNA movements following translocation and/or sample heterogeneity). These values are virtually identical to those found for translocation using either a proflavin-labeled derivative of tRNA$^{fMet}$ and unlabeled fMetPhe-tRNA$^{Phe}$ or a proflavin-labeled derivative of fMetPhe-tRNA$^{Phe}$ and unlabeled tRNA$^{fMet}$ (Pan et al., 2007), demonstrating the functionality of Cy-labeled derivatives in translocation.

In Pan et al. (2007) evidence was presented to the effect that the first phase of reaction corresponds to the formation of an intermediate complex (INT) in which the two tRNAs adopt hybrid orientations, with tRNA$^{fMet}$ in a P/E site and fMetPhe-tRNA$^{Phe}$ in an A/P site. It was also shown that viomycin allowed tRNA$^{fMet}$ movement into a P/E hybrid site, while blocking fMetPhe-tRNA$^{Phe}$ in the A-site. It is shown herein that added viomycin allows only a very small drop in FRET efficiency, with an apparent rate constant (16±2 s$^{-1}$) similar to that of the first phase of translocation, and that formation of INT from PRE also occurs with little change in FRET efficiency. These results imply that the distance between the core regions of the two tRNAs, to which the Cy dyes are attached, undergoes little change either during migration of tRNA$^{fMet}$ from the P- to the P/E site, or during INT complex formation from PRE complex. These results are consistent with the hypothesis that INT complex formation from PRE complex primarily involves movements of the flexible 3'-single-stranded regions of the tRNAs, whereas INT to POST conversion requires the considerable distance change between the tRNA cores that accompanies overall PRE to POST conversion.

Poly(U) Dependent Poly(Phe) Synthesis.

Figure 8:
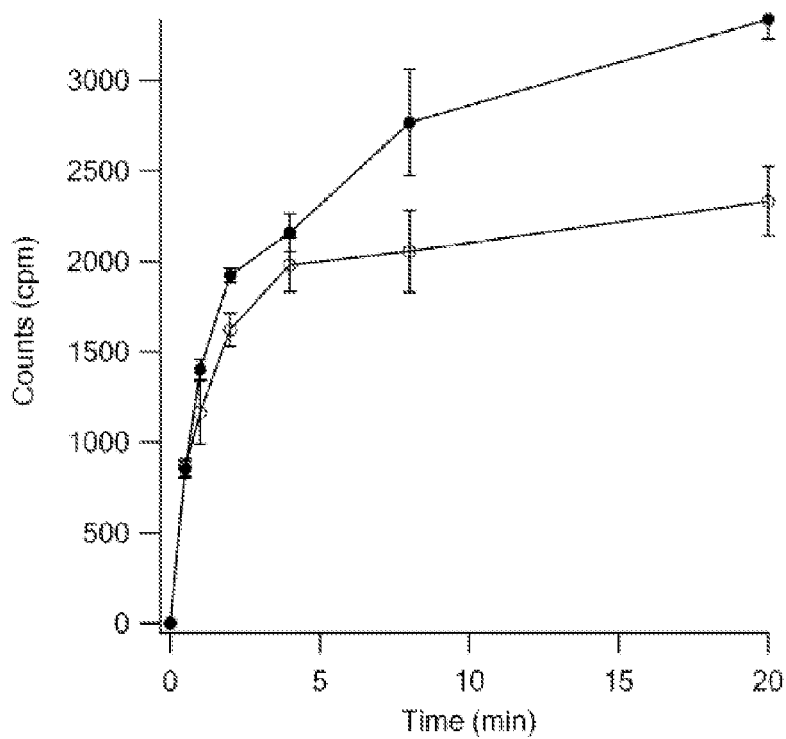
FIG. 8 provides data from a study of the activity of Cy3-tRNAPhe using a poly(Phe) assay.

Poly(Phe) synthesis by poly(U)-programmed ribosomes was conducted in parallel with both unlabeled Phe-tRNA$^{Phe}$ and Phe-tRNA$^{Phe}$(Cy3). The results obtained (FIG. 8) shows that both tRNAs have similar activity during the initial, rapid phase of reaction, although the labeled tRNA is less active in the slower second phase of reaction. In FIG. 8, each data point is the average of two independent experiments.

Example 8

Materials and Methods

Enzyme and tRNA.

The bacterial expression clone of yeast Dus1p with a C-terminal His tag was a gift of Dr. Eric Phiziky (U. Rochester). The fusion protein was purified from E. coli BL21(DE3) by sonication (in 20 mM Tris-HCl, pH 7.5, 50 mM NaCl, 4 mM MgCl$_2$, and 10% glycerol), binding to the His-link metal affinity resin (in the sonication buffer), and elution by 200 mM imidazole. Protein concentration was determined by the Bradford assay. The purified Dus1p enzyme was stored in 20 mM Tris-HCl, pH 7.5, 2 mM EDTA, 4 mM MgCl$_2$, 1 mM DTT, 50 mM NaCl, and 50% glycerol at −20° C. The gene for E. coli tRNA$^{Pro/UGG}$ was cloned into the pTFMa vector. Restriction of the gene with BstN1 provided a template for in vitro transcription by T7 RNA polymerase (Hou, 1993). The transcript was purified by a denaturing PAGE, visualized by UV shadowing, and extracted from the gel into TE (10 mM Tris-HCl, pH 8.0, 1 mM EDTA). The concentration of the transcript was determined by absorption at 260 nm, based on 10D=40 μg/mL tRNA.

Modification of tRNA Transcript by Purified Dus1p.

The tRNA transcript (in 20 concentrations) was heat-cooled before use in a typical Dus1p reaction containing 100 mM Tris-HCl, pH 8.0, 100 mM NH$_4$Ac, 5 mM MgCl$_2$, 2 mM dithiothreitol (DTT), 0.1 mM EDTA, 1 mM β-NADH (Sigma N1161), 1 mM NADPH (Sigma N6505), 250 μM FAD (Sigma F6625), and purified Dus1p (~5 μM) in a total volume of 50 μL. After incubation at 30° C. for at least 40 min, the tRNA transcript was purified by phenol extraction and ethanol precipitation.

Primer Extension.

Indicated amounts of tRNA were denatured in 0.1 M KOH at 37° C. for 20 min, and then neutralized with an equal volume of 5× annealing buffer (250 mM Tris-HCl, pH 8.3, 150 mM NaCl, 50 mM DTT). The tRNA (0.6 or 1.2 μg) was subjected to primer extension with AMV reverse transcriptase (2 units, Roche) at 42° C. for 30 min. The primer (6 pmole) was 5' labeled with γ-$^{32}$P-ATP by T4 polynucleotide kinase and hybridized to the tRNA substrate. The reaction was stopped by phenol/chloroform extraction, ethanol precipitated, and analyzed on a 12% PAGE/7M urea gel.

Rhodamine Labeling of tRNA.

Fluorescent labeling of tRNA with rhodamine was performed in the dark. Rhodamine 110 (Fluka #83695) was dissolved in 8 mg/mL in methanol, stored in the dark at −20° C. In a 20 µL reaction, the D-containing tRNA transcript (1800 pmole in 40 mM Tris-HCl, pH 7.5) was treated with $NaBH_4$ (100 mg/mL in 10 mM KOH) at a final concentration of 10 mg/mL for 60 min at room temperature on a shaker. The reaction was stopped by lowering the pH to 4-5 by gradually adding 6 M acetic acid. After the tRNA was precipitated and washed, it was resuspended in the order of 5 µL water, 85 µL of 0.1 M $NaCO_2H$ (pH 3.0), and 10 µL rhodamine 110 (0.022 M) and incubated at 37° C. for 90 min. The reaction was then adjusted to pH 7.5 by addition of 2 M Tris-HCl, pH 8.5. The tRNA was phenol extracted (pH 4.3), ethanol precipitated, and resuspended in water. Absorption was determined at 260 nm and 512 nm. Fluorescent labeling of tRNA with proflavin was performed in an essentially identical manner, following Wintermeyer & Zachau (1979), except that incubation at 37° C. was for 45 min.

Colorimetric Assay for Dihydrouridine.

The assay was performed as previously described (Jacobson & Hedgcoth, 1970) with some modifications. The D-containing tRNA (at various concentrations in 100 µL of water) was hydrolyzed by adding 10 µL of 1 M KOH and incubating at 37° C. for 30 min. The reaction was then neutralized by adding 50 µL of concentrated $H_2SO_4$, followed by 100 µL of a 1:1 mixture (v:v) of 3% diacetyl monoxime (2,3-butanedione 2-oxime, Fluka #31550) and saturated N-phenyl-p-phenylenediamine-HCl (200 mg (Fluka #07920) in 100 mL 10% ethanol). Ureido groups were exposed by heating the reaction at 95° C. for 5 min, then at 50° C. for 5 min. A solution of 100 µL of 1 mM $FeCl_3$ in concentrated $H_2SO_4$ was added to react with the ureido group. After the reaction cooled to room temperature, absorption was read at 550 nm. A control sample without tRNA was performed in parallel and used as a blank.

Purification of Rhodamine-Labeled tRNA.

The transcript of E. coli $tRNA^{Pro/UGG}$ labeled with rhodamine (880 pmole) was hybridized to a complementary chimeric oligonucleotide (1000 pmole) 5'-mU-mG-mC-mG-mC-mU-mA-mC-CAAG-mC-mU-mG-mC-mG-3', where "m" designates a 2'-O-methyl backbone (Hou et al., 2006). After annealing, the mixture (in 40 µL) and was digested with purified E. coli RNase H (50 µM) at 37° C. for 1 hour. The RNase H-resistant labeled transcript was separated from the RNase H-cleaved unlabeled transcript by 12% PAGE/7M urea on a BioRad minigel apparatus. The labeled transcript was extracted from the gel, ethanol precipitated, and resuspended in TE.

Fluorescence Measurement of Rhodamine-Labeled tRNA.

The emission spectrum of purified rhodamine-labeled E. coli $tRNA^{Pro/UGG}$ (0.012 µM in water) was recorded from 510 to 600 nm using an excitation wavelength of 498 nm in a model QM-4 fluorimeter (Photon Technology International). The rhodamine-labeled native yeast $tRNA^{Phe}$ was run as a control.

Aminoacylation of tRNA.

Aminoacylation with proline was carried out as described (Lipman et al., 2002), using the purified D. radiodurans ProRS (Zhang & Hou, 2004) at 1.0 µM for the unlabeled transcript of E. coli $tRNA^{Pro/UGG}$ (2.0 µM) and at 10.0 µM for the rhodamine-labeled transcript (2.0 µM). Reactions were incubated at 37° C. and aliquots were removed at various time intervals and precipitated in 5% TCA. Aminoacylation with phenylalanine was performed in similar conditions, but with 30 µM phenylalaine (870.3 dpm/pmol), 100 mM Tris-HCl (pH 8.0), 10 mM ATP, 50 mM $Mg(OAc)_2$, 2.5 mM EDTA (pH 8.0), 3 mM β-mercaptoethanol, and 7 mg/mL crude synthetase (~100 µM) at 37° C. for 20 min.

Poly(Phe) Assay.

Ribosomes 70S (15 pmol) were programmed with 15 mg polyU, E. coli $^3H$—AcPhe-$tRNA^{Phe}$ in 15 µL reaction buffer (50 mM Tris-HCl (pH 7.5), 70 mM $NH_4Cl$, 10 mM $Mg(OAc)_2$, 1 mM DTT) for 5 min at 37° C. Then 30 pmol EF-Tu, 30 pmol EF-G, 180 pmol yeast $^{14}C$-Phe-$tRNA^{Phe}$, 30 nmol GTP, 25 nmol phosphoenolpyruvate, 0.25 mg pyruvate kinase, 140 nmol β-mercaptoethanol were added to make a final volume of 50 µL. The mixture was then aliquoted into 4 µL portions for each point for acid precipitation.

Additional Labeling, Charging and Purification Procedures.

Reduction of $tRNA^{fMet}$ and $tRNA^{Phe}$ was performed by incubating 2.5 mg/ml tRNA, 10 mg/ml $NaBH_4$ (dissolved in small volume of 10 mM KOH) in 40 mM Tris-HCl (pH 7.5) at 0° C. for 60 min. 3 times of ethanol precipitation was followed to remove the extra $NaBH_4$. To label the tRNAs the dried pellets were dissolved in 40 µl of 0.1 M sodium formate (pH 3.7), and mixed with 10 µl of 200 mM Cy3- or Cy5-hydrazide in DMSO, and incubated at 37° C. for 2 hr, followed by drying in the vacuum, 2 times of extraction with buffer saturated phenol and 2 times of ethanol precipitation at pH 6.0 to remove the extra dye.

$tRNA^{fMet}$ (labeled or unlabeled) was charged and formylated by incubating 20 $tRNA^{fMet}$, 80 µM [$^{35}S$]-methionine, 720 µM folinic acid (as a formyl donor), and 1/10 volume of crude E. coli aminoacyl-tRNA synthetases (containing formyl transferase) in 100 mM Tris-HCl (pH 7.8), 4 mM ATP, 20 mM $MgCl_2$, 1 mM EDTA, 10 mM KCl, and 7 mM 2-mercaptoethanol at 37° C. for 20 min. Yeast $tRNA^{Phe}$ (labeled, unlabeled, or $NaBH_4$ treated) was charged by incubating 20 µM $tRNA^{Phe}$, 80 04 [$^3H$]-phenylalanine, 1/10 volume of partially purified yeast synthetase in 100 mM Tris-HCl (pH 8.0), 10 mM ATP, 50 mM $MgAc_2$, 2.5 mM EDTA, 3 mM 2-mercaptoethanol at 37° C. for 20 min. For $tRNA^{fMet}$ Cy5 labeling was performed before charging. For $tRNA^{Phe}$ because of the low charging efficiency of Cy3-$tRNA^{Phe}$ a modified protocol was used for later experiments, in which the $NaBH_4$-treated $tRNA^{Phe}$ was charged first, followed by HPLC separation of charged from uncharged $tRNA^{Phe}$ (see below), and then labeled. $tRNA^{Lys}$ was charged with pure His-tagged E. coli Lys-RS, purified on a Ni-NTA (Qiagen) column, by incubating 20 µM $tRNA^{Lys}$, [$^{14}C$]lysine, and 1 µM Lys-RS in 100 mM Tris-HCl (pH 7.8), 4 mM ATP, 20 mM $MgCl_2$, 1 mM EDTA, and 7 mM 2-mercaptoethanol at 37° C. for 10 min. Purification of the charge tRNAs were carried out on FPLC using a MonoQ column with a gradient of 0-1 M NaCl in 50 mM Na acetate (pH 5.0).

HPLC purification of Phe-$tRNA^{Phe}$ was conducted on a phenyl reverse-phase column (4.6×250 mm), with a gradient of 0-24% methanol in 20 mM $NH_4Ac$ (pH 5.5) and 50 mM NaCl. Phe-$tRNA^{Phe}$ formed after $NaBH_4$ treatment had essentially the same profile has the untreated Phe-$tRNA^{Phe}$. To purify labeled $tRNA^{fMet}$ or $tRNA^{Phe}$ from unlabeled tRNA a Mono-Q anion-exchange column was used on FPLC with a gradient of 0.5-0.9 M NaCl in 50 mM NaAc (pH 6.0). The final product of Cy5-fMet-$tRNA^{fMet}$ was 0.70-0.75 Cy5/$tRNA^{fMet}$, and 590 pmol/A260, and Cy3-Phe-$tRNA^{Phe}$ was 1.0 Cy3/$tRNA^{Phe}$, and 1190 pmol/A260.

Sample Preparation.

Tight-coupled ribosomes from E. coli MRE600 cells, mRNA022, unlabeled fMet-$tRNA^{fMet}$ and Phe-$tRNA^{Phe}$, and cloned E. coli His-tagged proteins EF-G, EF-Tu, IF1, IF2, and IF3 were prepared as described (Pan et al., 2008). mRNA-MFK was ordered from Dharmacon with the following sequence: GGG AAG GAG GUA AAA AUG UUU AAA CGU AAA UCU ACU. E. coli tRNA$^{fMet}$, tRNA$^{Lys}$, and yeast tRNA$^{Phe}$ were obtained from Chemical Block.

30SIC Formation.

The concentrations given are final. For IF2-Cy3 fluorescence change 0.45 μM each of fMet-tRNA$^{fMet}$, IF1, and IF3, 0.90 μM mRNA022, 100 μM GTP, and 0.30 μM 30S were preincubated at 37° C. for 15 min, and then rapidly mixed with 0.15 μM Cy3-IF2 in buffer A at 20° C. on a stopped flow apparatus, excited at 530 nm and monitored through a bandpass 550±10 nm filter. For Cy5-fMet-tRNA$^{fMet}$ change 0.45 μM each of IF1, IF2, and IF3, 0.90 μM mRNA022, 100 μM GTP, and 0.30 μM 30S were incubated at 37° C. for 15 min, before rapidly mixed with 0.15 μM Cy5-fMet-tRNA$^{fMet}$ in buffer A at 20° C., excited at 650 nm and monitored via a bandpass 680±10 nm filter.

Complex Formation.

70SIC was formed by incubating 2 μM 70S ribosome, 8 μM mRNA-MFK, 3 μM each of IF1, IF2, IF3, and fMet-tRNA$^{fMet}$, and 1 mM GTP in Buffer A (50 mM Tris-HCl (pH 7.5), 70 mM NH$_4$Cl, 30 mM KCl, 7 mM MgCl$_2$, 1 mM DTT) for 25 min at 37. TC was formed by incubating 6 EF-Tu, 3 μM Phe-tRNA$^{Phe}$, 1 mM GTP, 1.5 mM phosphoenolpyruvate, and 0.5 mg/L pyruvate kinase in buffer A for 5 min at 37° C. PRE complex was formed by incubating 1 μM 70SIC with 1.5 μM TC for 0.5 min at 37° C., and purified by centrifugation through a 1.1 M sucrose cushion (450,000 g, 40 min, 4° C.) in Buffer B (same as buffer A but with 20 mM MgCl$_2$). The pellet was resuspended in buffer C (20 mM HEPES-KOH (pH 7.6 at 0° C.), 4.5 mM MgAc$_2$, 4 mM 2-mercaptoethanol, 150 mM NH$_4$Ac, 0.05 mM spermine, and 2 mM spermidine) to a concentration of about 5 μM, and stored in a −80° C. freezer before being used.

FRET Measurements.

The steady state fluorescence spectra of 0.1 μM PRE, POST (PRE+0.5 uM EF-G+1 mM GTP), and POST2 (PRE+0.5 uM EF-G, 1 mM GTP, 0.3 uM [$^{14}$C]-Lys-tRNA$^{Lys}$ and 0.5 uM EF-Tu) complexes in buffer C were measured on a Fluorolog-3 spectrofluorometer (Horiba JobinYvon) with an excitation wavelength of 518 nm. Each trace is an average of 3 traces. Experiments with both donor Cy3-Phe-tRNA$^{Phe}$, and acceptor Cy5-fMet-tRNA$^{fMet}$ (DA) were run in parallel with donor alone (DU) or acceptor alone (UA).

For rapid kinetics FRET, PRE complex was rapidly mixed with 2 μM EF-G.GTP in buffer A at 25° C. on a SX.18MV stopped-flow spectrofluorometer (Applied Photophysics). Buffer A is used here to compare with previous results (Pan, 2007). The excitation wavelength was 518 nm. Donor was monitored using 570±10 nm bandpass filter and the acceptor was monitored using 680±10 nm bandpass filter. Correction was made by FRET=DA−DU−UA for acceptor change, and FRET=(DA−UA)/DU for donor change. A lag and two exponential phases are seen in both the donor increase and acceptor decrease traces. These two traces are fit globally by Scientist using A→B→C→D, where fluorescence values of A and B are set to be identical. The acceptor trace in the presence of viomycin (100 μM) is fit by a single-exponential term plus a slope term.

Poly(Phe) Assay.

Assay was carried out in buffer D (20 mM Tris-HCl (pH 7.6), 200 mM NH$_4$Cl, 10 mM MgAc$_2$), and the concentrations given below are final concentrations. Initiation complex was formed by mixing poly(U) 0.3 μg/ul, 0.3 μM 70S ribosome, and 0.36 μM [$^3$H]—AcPhe-tRNA$^{Phe}$ at 37° C. for 5 min, and then mixed with 2.8 μM 2-mercaptoethanol, 0.005 mg/ml pyruvate kinase, 0.6 μM GTP, 4 μM [$^3$H]-Phe-tRNA$^{Phe}$ (Cy3 labeled or unlabeled), 0.6 μM EF-G in a volume of 50 μl. 0.6 μM EF-Tu was added to initiate the reaction at 37° C., and aliquots were taken at time points and added to 0.3 ml 5% TCA, heated to 95° C. for 15 min, cooled on ice and filtered through a nitrocellulose filter with 5×1 ml washes with 5% cold TCA. A point was taken before addition of EF-Tu as the background.

Distance Calculation.

Equation (1) is used to calculate distance between the two fluorophores. $R_0$ is the Förster distance of this pair of donor and acceptor at which the FRET efficiency is 50%. $R_0$ of Cy3 and Cy5 is assumed to be 50 Å. E is the FRET efficiency calculated by relative donor decrease (last column in Table 2, supra) and a correction factor of 0.75 (labeling efficiency of Cy5-tRNA$^{fMet}$).

$$r = R_0 \left(\frac{1}{E} - 1\right)^{1/6} \tag{1}$$

REFERENCES CITED

Betteridge T, Liu H, Gamper H, Kirillov S, Cooperman B S, Hou Y M. Fluorescent labeling of tRNAs for dynamics experiments. RNA. 2007 September; 13(9):1594-601.

Bieling P, Beringer M, Adio S, Rodnina M V. Peptide bond formation does not involve acid-base catalysis by ribosomal residues. Nat Struct Mol. Biol. 2006 May; 13(5):423-8.

Bishop A C, Xu J, Johnson R C, Schimmel P, de Crecy-Lagard V. 2002. Identification of the tRNA-dihydrouridine synthase family. J Biol Chem 277:25090-25095.

Blanchard S C, Kim H D, Gonzalez R L, Jr., Puglisi J D, Chu S. 2004a. tRNA dynamics on the ribosome during translation. Proc Natl Acad Sci USA 101:12893-12898.

Blanchard S C, Gonzalez R L, Kim H D, Chu S, Puglisi J D. 2004b. tRNA selection and kinetic proofreading in translation. Nat Struct Mol Biol 11:1008-1014.

Boonacker E, Van Noorden C. 2001. Enzyme cytochemical techniques for metabolic mapping in living cells with special reference to proteolysis. J Histochem Cytochem 49:1473-1486.

Cerutti P, Miller N. 1967. Selective reduction of yeast transfer ribonucleic acid with sodium borohydride. J Mol Biol 26:55-66.

Cochella L, Green R. 2005. An active role for tRNA in decoding beyond codon:anticodon pairing. Science 308:1178-1180.

Grigoriadou C, Marzi S, Kirillov S, Gualerzi C O, Cooperman B S. A quantitative kinetic scheme for 70 S translation initiation complex formation. J Mol. Biol. 2007a Oct. 26; 373(3):562-72.

Grigoriadou C, Marzi S, Pan D, Gualerzi C O, Cooperman B S. The Translational Fidelity Function of IF3 During Transition from the 30 S Initiation Complex to the 70 S Initiation Complex. J Mol. Biol. 2007b Oct. 26; 373(3):551-61.

Hirsh D. 1971. Tryptophan transfer RNA as the UGA suppressor. J Mol Biol 58:439-458.

Horobin R W, Stockert J C, Rashid-Doubell F. 2006. Fluorescent cationic probes for nuclei of living cells: why are they selective? A quantitative structure-activity relations analysis. Histochem Cell Biol 126:165-175.

Hou Y M. 1993. The tertiary structure of tRNA and the development of the genetic code. Trends Biochem Sci 18:362-364.

Hou Y M, Li Z, Gamper H. 2006. Isolation of a site-specifically modified RNA from an unmodified transcript. *Nucleic Acids Res* 34:e21.

Jacobson M, Hedgcoth C. 1970. Determination of 5,6-dihydrouridine in ribonucleic acid. *Anal Biochem* 34:459-469.

Jencks, W. P. Mechanism and catalysis of simple carbonyl group reactions. Prog. Phys. Org. Chem. 1964, 2, 63-128.

Korostelev A, Trakhanov S, Laurberg M, Noller H F. 2006. Crystal structure of a 70S ribosome-tRNA complex reveals functional interactions and rearrangements. *Cell* 126: 1065-1077.

Lipman R S, Wang J, Sowers K R, Hou Y M. 2002. Prevention of mis-aminoacylation of a dual-specificity aminoacyl-tRNA synthetase. *J Mol Biol* 315:943-949.

Lee L G, Spurgeon S L, Heiner C R, Benson S C, Rosenblum B B, Menchen S M, Graham R J, Constantinescu A, Upadhya K G, Cassel J M., New energy transfer dyes for DNA sequencing, 1997, Nucleic Acids Res. 1997 25:2816-22.

Levrand B, Fieber W, Lehn J-M, and Herrmann A. Controlled Release of Volatile Aldehydes and Ketones from Dynamic Mixtures Generated by Reversible Hydrazone Formation Helv Chim Acta 2007 90: 2281-2314

Liu H, Musier-Forsyth K. 1994. *Escherichia coli* proline tRNA synthetase is sensitive to changes in the core region of tRNA(Pro). *Biochemistry* 33:12708-12714.

McIntosh B, Ramachandiran V, Kramer G, Hardesty B. Initiation of protein synthesis with fluorophore-Met-tRNA(f) and the involvement of IF-2. Biochimie. 2000 82:167-74.

Munro J B, Altman R B, O'Connor N, Blanchard S C. Identification of two distinct hybrid state intermediates on the ribosome. *Mol. Cell.* 2007; 25:505-17.

Negrutskii B S, Deutscher M P. 1991. Channeling of aminoacyl-tRNA for protein synthesis in vivo. *Proc Natl Acad Sci USA* 88:4991-4995.

Pan D, Kirillov S, Cooperman B. 2007. Kinetically competent intermediate(s) in the translocation step of protein synthesis. *Mol Cell*, in press.

Pan D, Kirillov S, Zhang C M, Hou Y M, Cooperman B S. 2006. Rapid ribosomal translocation depends on the conserved 18-55 base pair in P-site transfer RNA. *Nat Struct Mol Biol* 13:354-359.

Pan D, Zhang C M, Kirillov S, Hou Y M, Cooperman B S. Perturbation of the tRNA tertiary core differentially affects specific steps of the elongation cycle. J Biol. Chem. 2008 Apr. 30. [Epub ahead of print] PMID: 18448426.

Pape, T., Wintermeyer, W., and Rodnina, M. V., Complete kinetic mechanism of elongation factor Tu-dependent binding of aminoacyl-tRNA to the A site of the *E. coli* ribosome, 1998, Embo J. 17:7490-7497.

Qin, H., Grigoriadou, C., and Cooperman, B. S. (manuscript in preparation).

Sako Y, Usuki F, Suga H, A novel therapeutic approach for genetic diseases by introduction of suppressor tRNA Nucleic Acids. 2006. Symp. Ser., 50, 239-240.

Sampson J R, DiRenzo A B, Behlen L S, Uhlenbeck O C. 1989. Nucleotides in yeast tRNAPhe required for the specific recognition by its cognate synthetase. *Science* 243: 1363-1366.

Savelsbergh A, Katunin V I, Mohr D, Peske F, Rodnina M V, Wintermeyer W. 2003. An elongation factor G-induced ribosome rearrangement precedes tRNA-mRNA translocation. *Mol Cell* 11:1517-1523.

Scala-Valero C Doizi D Guillaumet G, Synthesis of Isomers of Rhodamine 575 and Rhodamine 6G as New Laser Dyes, 1999, Tet Lett 40 4803-4806.

Selmer M, Dunham C M, Murphy F V t, Weixlbaumer A, Petry S, Kelley A C, Weir J R, Ramakrishnan V. 2006. Structure of the 70S ribosome complexed with mRNA and tRNA. *Science* 313:1935-1942.

Snustad D. P and Simmons M J 2003 Principles of Genetics John Wiley & Sons, Hoboken, N.J. Sprinzl M, Horn C, Brown M, Ioudovitch A, Steinberg S. 1998. Compilation of tRNA sequences and sequences of tRNA genes. *Nucleic Acids Res* 26:148-153.

Thiebe R, Zachau H G. A specific modification next to the anticodon of phenylalanine transfer ribonucleic acid. Eur J. Biochem. 1968 5:546-55.

Westhof E. 2006. The ribosomal decoding site and antibiotics. *Biochimie* 88:931-933.

Wintermeyer W, Zachau H G. Replacement of Y base, dihydrouracil, and 7-methylguanine in tRNA by artificial odd bases. FEBS Lett. 1971 18:214-218.

Wintermeyer W, Zachau H G. 1974. Replacement of odd bases in tRNA by fluorescent dyes. *Methods Enzymol* 29:667-673.

Wintermeyer W, Zachau H G. 1979. Fluorescent derivatives of yeast tRNAPhe. *Eur J Biochem* 98:465-475.

Woolhead C A, McCormick P J, Johnson A E: Nascent membrane and secretory proteins differ in FRET-detected folding far inside the ribosome and in their exposure to ribosomal proteins. Cell 2004, 116:725-736.

Xing F, Hiley S L, Hughes T R, Phizicky E M. 2004. The specificities of four yeast dihydrouridine synthases for cytoplasmic tRNAs. *J Biol Chem* 279:17850-17860.

Yusupov et al., Crystal Structure of the Ribosome at 5.5 Å Resolution, 2001, Science 5518(292), 883-896.

Zhang C-M, Hou Y-M. 2004. Synthesis of cysteinyl-tRNA-Cys by a prolyl-tRNA synthetase. *RNA Biology* 1:35-41.

What is claimed:

1. A method for labeling a transfer RNA molecule comprising:
providing a substitution comprising a fluorophore bearing a hydrazide functional group at the dihydrouracil component of a dihydrouridine of said transfer RNA by incubating said transfer RNA in a reaction medium comprising at least 40 mM of said fluorophore at about pH 3.7 for about 2 hours.

2. The method according to claim 1, wherein the transfer RNA has at least one uridine in its D loop, and further comprising converting said uridine to dihydrouridine prior to substituting at said uridine component with said fluorophore.

3. The method according to claim 1 further comprising loading onto the 3' end of said transfer RNA an amino acid corresponding to a triplet nucleotide sequence that base-pairs to the anticodon sequence of said transfer RNA.

4. The method to claim 1 further comprising subjecting said transfer RNA to conditions effective to load onto the 3' end of said transfer RNA an amino acid corresponding to a triplet nucleotide sequence that base-pairs to the anticodon sequence of said transfer RNA.

5. The method of claim 1 wherein dihydrouridine is subjected to reducing conditions.

6. The method of claim 5 wherein the reducing conditions comprise reacting with borohydride.

7. A nucleic acid composition comprising a transfer RNA molecule including a fluorophore substitution at the dihydrouracil component of a dihydrouridine in a D loop of the transfer RNA, the fluorophore bearing a hydrazide functional group, and the fluorophore-labeled transfer RNA having been prepared by incubating said transfer RNA in a reaction medium comprising at least 40 mM of said fluorophore at about pH 3.7 for about 2 hours.

8. The composition of claim 7 wherein the dihydrouridine is a position U16, U17, U20, or U20b.

9. A method of assessing protein synthesis in a translation system that comprises a living cell comprising:
providing a tRNA having a fluorophore substitution at the dihydrouracil component of a dihydrouridine in a D loop of the tRNA, the fluorophore bearing a hydrazide functional group, and the fluorophore-labeled tRNA having been prepared by incubating said tRNA in a reaction medium comprising at least 40 mM of said fluorophore at about pH 3.7 for about 2 hours;
introducing the labeled tRNA into the translation system;
irradiating the translation system with electromagnetic radiation, thereby generating a fluorescence signal from said fluorophore;
detecting said fluorescence signal; and,
correlating said fluorescence signal to one or more characteristics of said protein synthesis in said translation system.

10. The method according to claim 9 wherein said fluorophore is a hydrazide comprising Cy3 hydrazide, Cy3.5 hydrazide, Cy5 hydrazide, Cy5.5 hydrazide, Alexa Fluor 488 hydrazide, Alexa Fluor 555 hydrazide, Alexa Fluor 568 hydrazide, Alexa Fluor 594 hydrazide, and Alexa Fluor 647 hydrazide, Texas Red hydrazide, Lucifer yellow hydrazide, C5-DMB-ceramide, $C_6$-phosphatidylinositol 5-phosphate, Cascade Blue hydrazide, or ATTO dye.

11. The method according to claim 9 wherein the translation system comprises a cell-free system.

12. The method according to claim 9 wherein the translation comprises a living cell.

13. The method according to claim 9 further comprising providing at least one additional fluorescently labeled translation component.

14. The method according to claim 13 wherein said fluorescently labeled translation component comprises a ribosome, a ribosomal protein, an initiation factor, an elongation factor, a messenger RNA, or a ribosomal RNA.

15. The method according to claim 13 wherein the fluorophore of said labeled tRNA and the fluorophore of said at least one additional fluorescently labeled component comprise a FRET pair, and wherein said detecting said fluorescence signal comprises detecting energy transfer between the fluorophore of said labeled tRNA and the fluorophore of said at least one additional fluorescently labeled component.

16. The method according to claim 1 wherein said fluorophore is a hydrazide comprising Cy3 hydrazide, Cy3.5 hydrazide, Cy5 hydrazide, Cy5.5 hydrazide, Alexa Fluor 488 hydrazide, Alexa Fluor 555 hydrazide, Alexa Fluor 568 hydrazide, Alexa Fluor 594 hydrazide, and Alexa Fluor 647 hydrazide, Texas Red hydrazide, Lucifer yellow hydrazide, C5-DMB-ceramide, $C_6$-phosphatidylinositol 5-phosphate, Cascade Blue hydrazide, or ATTO dye.

17. The method according to claim 9 wherein said fluorophore is a hydrazide comprising Cy3 hydrazide, Cy3.5 hydrazide, Cy5 hydrazide, Cy5.5 hydrazide, Alexa Fluor 488 hydrazide, Alexa Fluor 555 hydrazide, Alexa Fluor 568 hydrazide, Alexa Fluor 594 hydrazide, and Alexa Fluor 647 hydrazide, Texas Red hydrazide, Lucifer yellow hydrazide, C5-DMB-ceramide, $C_6$-phosphatidylinositol 5-phosphate, Cascade Blue hydrazide, or ATTO dye.

* * * * *

UNITED STATES PATENT AND TRADEMARK OFFICE
CERTIFICATE OF CORRECTION

| | | |
|---|---|---|
| PATENT NO. | : 8,785,119 B2 | Page 1 of 1 |
| APPLICATION NO. | : 12/664952 | |
| DATED | : July 22, 2014 | |
| INVENTOR(S) | : Barry S. Cooperman et al. | |

It is certified that error appears in the above-identified patent and that said Letters Patent is hereby corrected as shown below:

IN THE SPECIFICATION:

Column 1
Lines 4-10, after "STATEMENT OF GOVERNMENT SUPPORT," delete "The United States government may have rights in the invention described herein, which was made in part with funding from The National Institutes of Health, Grant Nos. GM66267 and GM71014." and insert -- This invention was made with government support under grant no. GM071014 and GM066267 awarded by the Nation Institutes of Health. The government has certain rights in the invention. --.

Signed and Sealed this
Tenth Day of February, 2015

Michelle K. Lee
*Deputy Director of the United States Patent and Trademark Office*